(12) United States Patent
Wiechmann et al.

(10) Patent No.: US 7,850,451 B2
(45) Date of Patent: *Dec. 14, 2010

(54) MODULAR SYSTEM FOR CUSTOMIZED ORTHODONTIC APPLIANCES

(75) Inventors: Dirk Wiechmann, Bad Essen (DE); Ralf Paehl, Melle (DE); Rüdger Rubbert, Berlin (DE); Thomas Weise, Berlin (DE)

(73) Assignee: 3M Innovative Properties Company, Saint Paul, MN (US)

(*) Notice: Subject to any disclaimer, the term of this patent is extended or adjusted under 35 U.S.C. 154(b) by 1627 days.

This patent is subject to a terminal disclaimer.

(21) Appl. No.: 10/897,149

(22) Filed: Jul. 22, 2004

(65) Prior Publication Data

US 2005/0003321 A1    Jan. 6, 2005

Related U.S. Application Data

(63) Continuation of application No. 10/075,676, filed on Feb. 13, 2002, now Pat. No. 6,776,614.

(51) Int. Cl.
*A61C 3/00* (2006.01)
(52) U.S. Cl. ......................................................... 433/24
(58) Field of Classification Search .................... 433/24, 433/213, 8; 700/98
See application file for complete search history.

(56) References Cited

U.S. PATENT DOCUMENTS

| | | | |
|---|---|---|---|
| 1,103,606 A | 7/1914 | Montag | |
| 1,163,196 A | 12/1915 | Angle | |
| 2,566,414 A | 7/1948 | Henry | |
| 2,908,974 A | 10/1959 | Stifter | |
| 3,250,003 A | 5/1966 | Collito | |
| 3,352,136 A | 11/1967 | Clarke | |
| 3,738,005 A | 6/1973 | Cohen et al. | |
| 3,922,787 A | 12/1975 | Fischer | |
| 3,936,939 A | 2/1976 | Faunce | |

(Continued)

FOREIGN PATENT DOCUMENTS

EP          0290247          9/1988

(Continued)

OTHER PUBLICATIONS

T. Creekmore, "Lingual orthodontics—Its renaissance", American Journal of Orthodontics and Denotfacial Orthopedics, Aug. 1989; vol. 96 No. 2, pp. 120-137.

(Continued)

*Primary Examiner*—Ralph A Lewis
*Assistant Examiner*—Edward Moran

(57) ABSTRACT

A set of customized orthodontic brackets are provided with slots that are arranged substantially parallel to the tooth surface. The archwire, in an as-manufactured condition, has a portion of substantial arcuate extent, which is canted relative to the occlusal plane. The brackets are designed on a computer as a combination of three-dimensional virtual objects comprising the virtual bracket bonding pad and a separate virtual bracket body retrieved from a library of virtual bracket bodies. The virtual brackets can be represented as a file containing digital shape data and exported to a rapid prototype fabrication device for fabrication of the bracket in wax or other material and casting the wax prototype in a suitable alloy. Other manufacturing techniques are also contemplated, including milling and laser sintering.

35 Claims, 11 Drawing Sheets

U.S. PATENT DOCUMENTS

| | | | |
|---|---|---|---|
| 4,184,259 A | 1/1980 | Sosnay | |
| 4,219,617 A | 8/1980 | Wallshein | |
| 4,243,386 A | 1/1981 | Kawacuchi | |
| 4,337,037 A | 6/1982 | Kurz | |
| 4,386,908 A | 6/1983 | Kurz | |
| 4,470,809 A | 9/1984 | Klepacki | |
| 4,504,225 A | 3/1985 | Yoshii | |
| 4,505,673 A | 3/1985 | Yoshii | |
| 4,575,337 A | 3/1986 | Fujita | |
| 4,656,860 A | 4/1987 | Orthuber | |
| 4,732,025 A | 3/1988 | Marlinga et al. | |
| 5,092,941 A | 3/1992 | Miura | |
| 5,136,515 A | 8/1992 | Helinski | |
| 5,139,419 A | 8/1992 | Andreiko et al. | |
| 5,248,257 A | 9/1993 | Cannon | |
| 5,275,031 A | 1/1994 | Whiteside | |
| 5,295,886 A | 3/1994 | Wildman | |
| 5,368,478 A | 11/1994 | Andreiko et al. | |
| 5,374,187 A * | 12/1994 | Vashi | 433/8 |
| 5,431,562 A | 7/1995 | Andreiko et al. | |
| 5,447,432 A | 9/1995 | Andreiko et al. | |
| 5,454,347 A | 10/1995 | Shibata et al. | |
| 5,454,717 A | 10/1995 | Andreiko et al. | |
| 5,456,600 A | 10/1995 | Andreiko et al. | |
| RE35,169 E | 3/1996 | Lemchen et al. | |
| 5,510,066 A | 4/1996 | Fink et al. | |
| 5,518,397 A | 5/1996 | Andreiko et al. | |
| 5,533,895 A | 7/1996 | Andreiko et al. | |
| 5,683,243 A | 11/1997 | Andreiko et al. | |
| 5,736,015 A | 4/1998 | Armentrout | |
| 5,879,158 A * | 3/1999 | Doyle et al. | 433/24 |
| 5,931,667 A | 8/1999 | Papandreas | |
| 5,975,893 A | 11/1999 | Chishti et al. | |
| 6,015,289 A * | 1/2000 | Andreiko et al. | 433/3 |
| 6,214,285 B1 | 4/2001 | Rubbert et al. | |
| 6,217,325 B1 | 4/2001 | Chishti et al. | |
| 6,227,850 B1 | 5/2001 | Chishti et al. | |
| 6,227,851 B1 * | 5/2001 | Chishti et al. | 433/24 |
| 6,250,918 B1 | 6/2001 | Sachdeva et al. | |
| 6,264,468 B1 | 7/2001 | Takemoto | |
| 6,264,469 B1 | 7/2001 | Moschik | |
| 6,293,791 B1 | 9/2001 | Weinstein | |
| 6,315,553 B1 | 11/2001 | Sachdeva et al. | |
| 6,318,995 B1 | 11/2001 | Sachdeva et al. | |
| 6,322,728 B1 | 11/2001 | Brodkin et al. | |
| 6,350,120 B1 | 2/2002 | Sachdeva | |
| 6,382,966 B1 | 5/2002 | Aknin | |
| 6,431,870 B1 | 8/2002 | Sachdeva et al. | |
| 6,464,496 B1 | 10/2002 | Sachdeva et al. | |
| 6,471,512 B1 | 10/2002 | Sachdeva et al. | |
| 6,612,143 B1 | 9/2003 | Butscher | |
| 6,632,089 B2 | 10/2003 | Rubbert et al. | |
| 6,648,640 B2 | 11/2003 | Rubbert | |
| 6,685,468 B1 | 2/2004 | Kesling | |
| 6,739,869 B1 * | 5/2004 | Taub et al. | 433/24 |
| 6,776,614 B2 | 8/2004 | Wiechmann et al. | |
| 6,846,179 B2 | 1/2005 | Chapouland et al. | |
| 6,928,733 B2 | 8/2005 | Rubbert et al. | |
| 6,936,939 B2 | 8/2005 | Ide et al. | |
| 6,988,889 B2 * | 1/2006 | Abels et al. | 433/24 |
| 7,037,108 B2 | 5/2006 | Chishti et al. | |
| 7,155,373 B2 * | 12/2006 | Jordan et al. | 703/1 |
| 7,188,421 B2 * | 3/2007 | Cleary et al. | 29/896.11 |
| 7,229,282 B2 | 6/2007 | Andreiko | |
| 7,240,528 B2 | 7/2007 | Weise et al. | |
| 7,335,024 B2 | 2/2008 | Wen | |
| 7,474,307 B2 | 1/2009 | Chishti et al. | |
| 2001/0002310 A1 * | 5/2001 | Chishti et al. | 433/24 |
| 2002/0010568 A1 * | 1/2002 | Rubbert et al. | 703/6 |
| 2002/0025503 A1 | 2/2002 | Chapoulaud et al. | |
| 2002/0028417 A1 | 3/2002 | Chapouland | |
| 2003/0180678 A1 | 9/2003 | Kesling | |
| 2003/0224317 A1 * | 12/2003 | Andreiko et al. | 433/24 |
| 2004/0072120 A1 | 4/2004 | Lauren | |
| 2004/0086824 A1 | 5/2004 | Kesling | |
| 2004/0175669 A1 * | 9/2004 | Abels et al. | 433/24 |
| 2005/0003321 A1 | 1/2005 | Wiechmann et al. | |
| 2005/0158686 A1 | 7/2005 | Wiechmann et al. | |
| 2006/0127834 A1 | 6/2006 | Szwajkowski et al. | |
| 2007/0015104 A1 | 1/2007 | Wiechmann et al. | |
| 2007/0178423 A1 | 8/2007 | Rubbert | |
| 2007/0218419 A1 | 9/2007 | Rubbert | |

FOREIGN PATENT DOCUMENTS

| | | |
|---|---|---|
| EP | 290247 A2 | 9/1988 |
| EP | A-0 290 247 | 11/1988 |
| EP | 10/80697 | 3/2001 |
| EP | 1080697 | 3/2001 |
| FR | 2369828 | 11/1977 |
| WO | 9410935 A1 | 5/1994 |
| WO | WO 94/10935 A | 5/1994 |
| WO | WO 9410935 | 5/1995 |
| WO | 9858596 A1 | 12/1998 |
| WO | 0111969 A1 | 2/2001 |
| WO | WO 01/80761 | 11/2001 |

OTHER PUBLICATIONS

Geschaftsbereich Medizintechnik, Bending Art System, 1992, Germany.

Geschaftsbereich Medizintechnik, Bending Art System, 1994, Germany.

Fillion D.; "The Thickness Measurement System with the DALI Program;" Ramano R. Lingual orthodontics, Hamilton-London: Decker; pp. 175-184 (1998).

Fujita, K.; "Development of lingual-bracket technique;" J Jpn Orthod Soc; vol. 37, pp. 381-384 (1978).

Hiro T.; "Resin core indirect bonding system-improvement of lingual orthodontic treatment;" J Jpn Orthod Soc; vol. 57, pp. 83-91 (1998).

Huge, S.A.; "The customized lingual appliance set-up service (CLASS) system;" Ramano R Lingual orthodontics, Hamilton-London: Decker; pp. 163-173 (1998).

Wiechmann, D.; "Lingual orthodontics. Part 1: Laboratory procedure;" J Orofac OrthopjFortschr Kieferorthop; vol. 60 pp. 371-379 (1999).

Wiechmann, D.; "Lingual orthodontics. Part 2: Archwire fabrication;" J Orofac OrthopjFortschr Kieferorthop; vol. 60 pp. 416-426 (1999).

Wiechmann, D.; "A New Bracket System for Lingual Orthodontic Treatment Part 1: Theoretical Background and Development;" J Orofac OrthopjFortschr Kieferorthop 2002; Clinical Forum; pp. 234-245 (2002).

Weichmann, Dirk, A New Bracket System for Lingual Orthodontic Treatment, J Orofac Orthop 2003;64:372-88.

Weichmann, Dirk, A New Bracket System for Lingual Orthodontic Treatment, J Orofac Orthop 2002;63:234-45.

Weichmann, Dirk, et al., Customized Brackets and Archwires for Lingual Orthodontic Treatment, Am J Orthod Dentofacial Orthop 2003;124:593-99.

Mujagic, Magali, et al., Digital Design and Manufacturing of the Lingualcare Bracket System, J Clin. Orthod Jun. 2005;39:6:375-82.

Creekmore, T., "Lingual orthodontics—Its renaissance", American Journal of Orthodontics and Denotfacial Orthopedics, Aug. 1989; vol. 96, No. 2, pp. 120-137.

Wiechmann, D.; "Lingual Orthodontics. Part 1: Laboratory Procedure;" J Orofac OrthopjFortschr Kieferorthop; vol. 60, pp. 371-379 (1999).

Wiechmann, D.; "Lingual orthodontics. Part 2: Archwire fabrication;" J Orofac OrthopjFortschr Kieferorthop; vol. 60, pp. 416-426 (1999).

Wiechmann, D., "A New Bracket System for Lingual Orthodontic Treatment Part 2: First Clinical Experiences and Further Development," J Orofac Orthop 2003, No. 5, pp. 372-388.

Geyer Medizintechnik, "Marketing brochure distributed at German Annual Orthodontic Congress 1994", Berlin, German(facsimile, 8 pages).

Wiechmann, Dirk, et al., Customized Brackets and Archwires for Lingual Orthodontic Treatment, Am J Dentofacial Orthop 2003; 123:593-599.

Mujagic, Magali, "Digital Design and Manufacturing of the Lingualcare Bracket System," vol. 39: No. 6, pp. 375-382 (2005).

Kurz, Craven et al., Linqual Orthodontics: A Status Report Part 2 Research and Development, JCO Nov. 1982 (735-740), pp. 1-10.

TStamm, A Subjective comparison of two lingual bracket systems, European Journal of Orthondontics, 2005.

Hohoff, Comparison of 3 bonded lingual appliances by auditive analysis and subjective assessment, American Journal of Orthodotics and Dentofacial Orthopedics, pp. 737-745, Dec. 2003.

Rubbert, U.S. Appl. No. 11/893,632, filed Aug. 16, 2007.

Align Technology Presentation, found at (http://www.aligntechinsitute.com/files/ATEArchive/pdf/ATE.Jan.2009.Invasalign%20Assist%20ATE%20Jan%2009.pdf.

P. Ling, Article titled "Clinical Limitations of Invisalign," Clinical Practice, found at www.cda-adc.ca/jcda/vol.-73/issue-3/263.html, Apr. 2007.

G. Djeu, Article titled Outcome assessment of Invisalign and traditional orthodontic tratment compared with the American Board of Orthodontics objective grading system, American Journal of Orthodontics and Dentofacial Orthopedics, Sep. 2005.

Office Action dated Dec. 10, 2009 in co-pending U.S. Appl. No. 10/843,897.

Marketing brochure distributed at German Annual Orthodontic Congress 1994 by Geyer Nedizintechnick, Berlin, Germany 8 pages.

Printed Advertisement by Geyer Medizintechnik in Congress Program of German Annual Orthodontic Congress 1993; 1 page.

Creekmore, T.—Lingual Orthodontics—Ots renaissance—American Journal of Orthodontics and Dentofacial Orthopedics, 198 August; vol. 96, No. 2 pp. 120-137.

Stamm et al., A subjective comparison of two lingual bracket systems, European Journal of Orthodontics, 27, 2005, pp. 420-426.

Kurz, C.—Lingual Orthodontics: A Status Report Part 2 Research and Development; JCO, pp. 1-9 (1982).

Hohoff, et al., Comparison of 3 bonded lingual appliances by auditive analysis and subjective assessment, American Journal of Orthod Dentofacial Orthop, 2003, 124, pp. 737-745.

Partial File History of co-pending U.S. Appl. No. 10/843,897.

Partial File History of co-pending U.S. Appl. No. 11/522,674.

Partial File History of co-pending U.S. Appl. No. 11/749,860.

Partial File History of co-pending U.S. Appl. No. 11/899,632.

Partial File History of co-pending U.S. Appl. No. 11/583,103.

Align Technology Presentation, found at (http://www.aligntechinstitute.com/files/ATEArchive/pdf/ATE.Jan.2009.Invisalign%20Assist%DATE%Jan%2009.pdf.

Phan, et al. Article tilted Clinical Limitations of Invisaslign, Clinical Practice, found at www.cda-adc.ca/joda/vol.-73/issue-3/263.html, Apr. 2007.

Djeu, Outcome assessment of invisalign and traditional orthodontic treatment compared with the American Board of Orthodontics objective grading system, American Journal of Orthodontics and Dentofacial Orthopedics, Sep. 2005.

Marketing brochure distributed at German Annual Orthodontic Congress 1994 by Geyer Nedizintechnick, Berlin, Germany 8 pages.

Printed Advertisement by Geyer Medizintechnik in Congress Program of German Annual Orthodontic Congress 1993; 1 page.

* cited by examiner

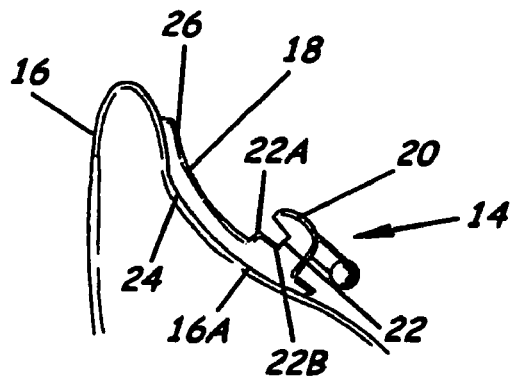
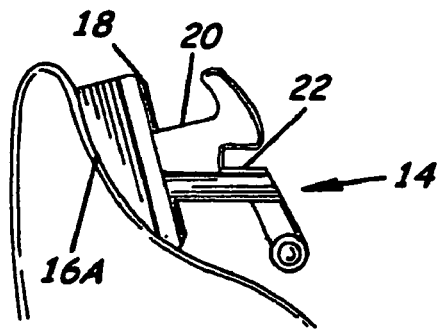
FIG. 3A.
FIG. 3B.
(PRIOR ART)
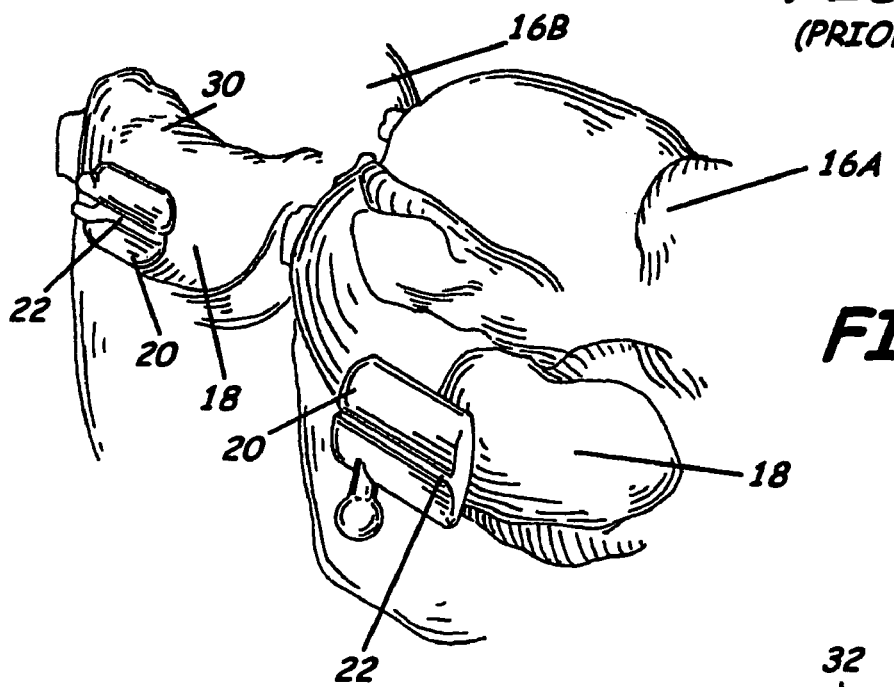
FIG. 4.
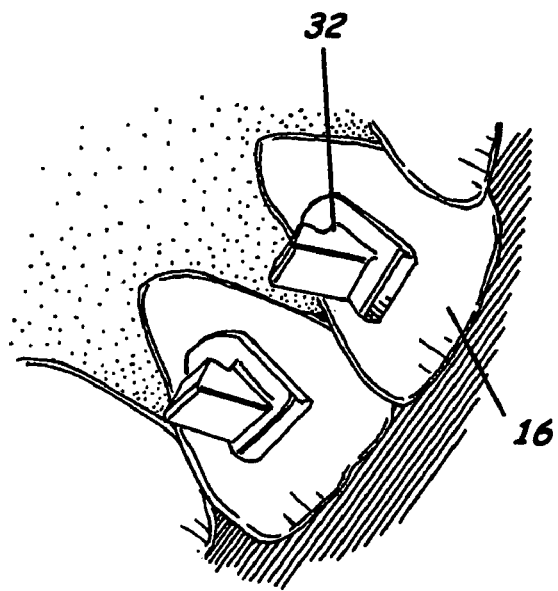
FIG. 5.

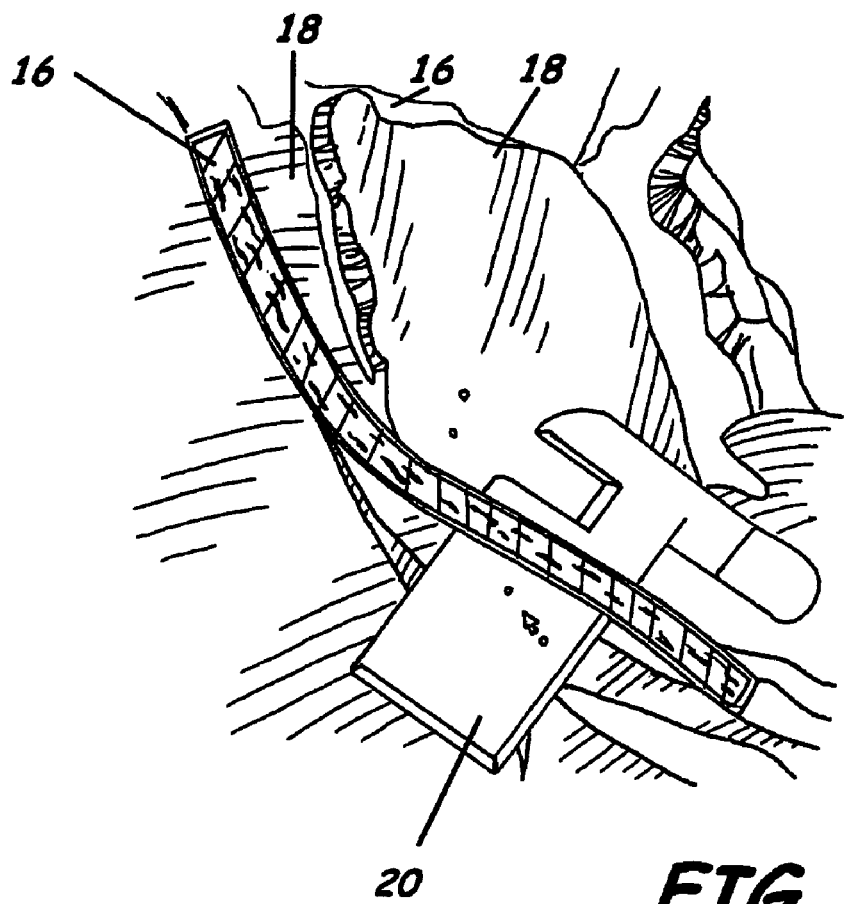
FIG. 12.
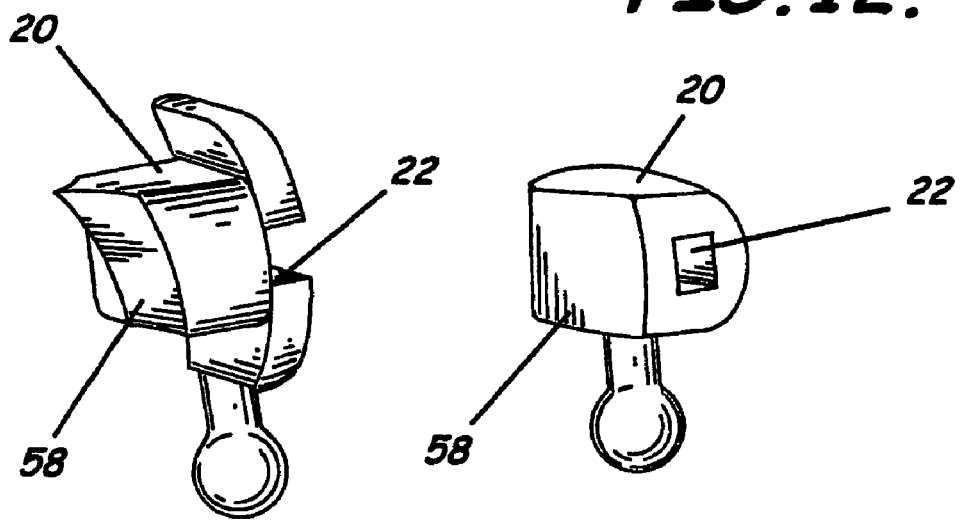
FIG. 13A.
FIG. 13B.

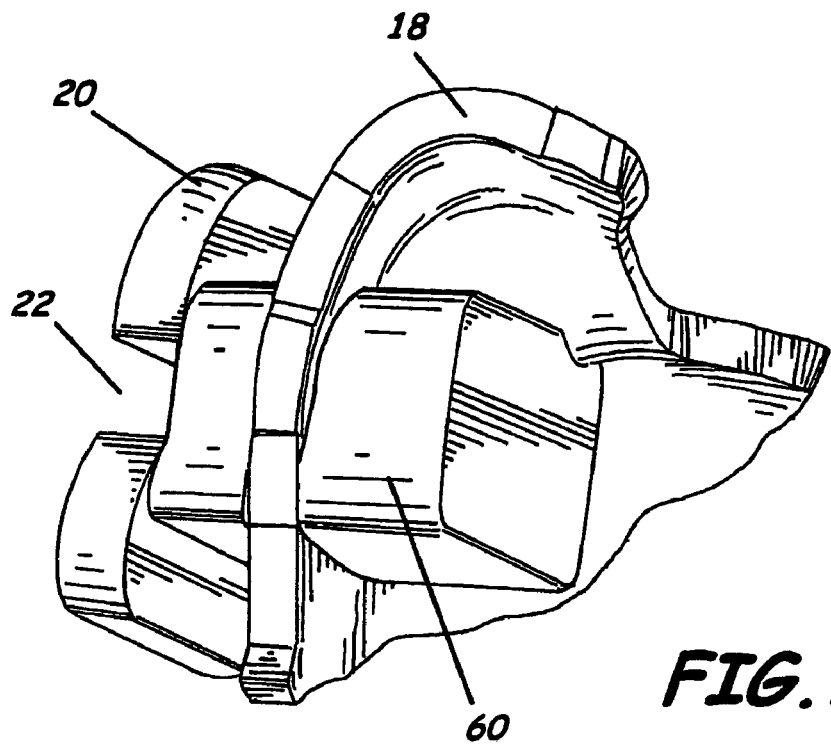
FIG.18A.
FIG.18B.
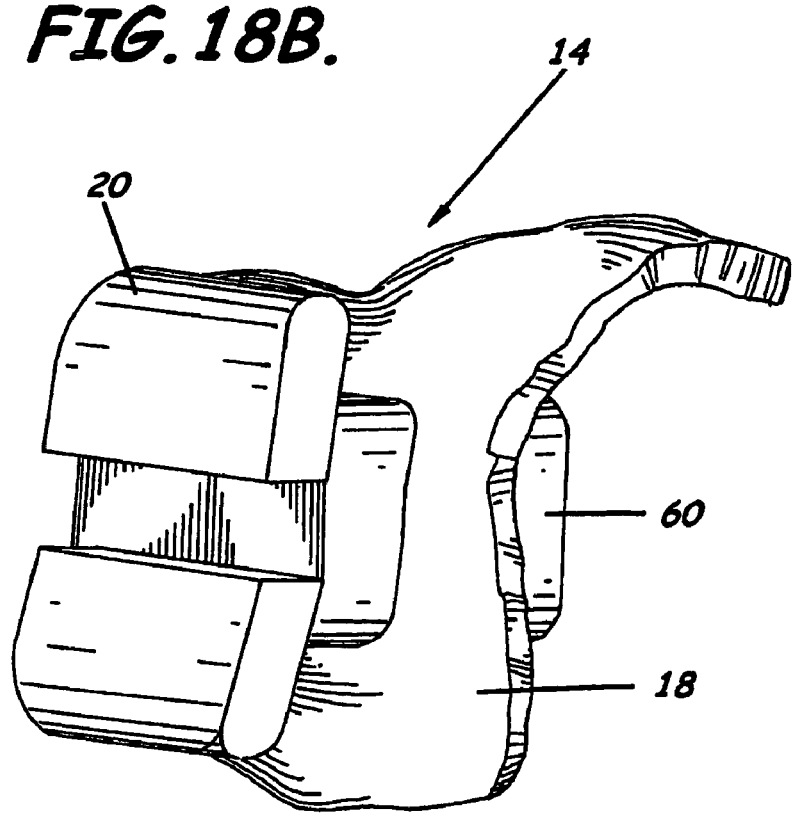

MODULAR SYSTEM FOR CUSTOMIZED ORTHODONTIC APPLIANCES

CROSS REFERENCE TO RELATED APPLICATIONS

This application is a continuation of and claims priority to U.S. patent application Ser. No. 10/075,676, filed Feb. 13, 2002, now U.S. Pat. No. 6,776,614, which is incorporated herein by reference in its entirety.

BACKGROUND OF THE INVENTION

A. Field of the Invention

This invention relates generally to the field of orthodontics. More particularly, the invention relates to methods for designing and manufacturing brackets and archwires for purposes of straightening the teeth of a patient, and novel brackets and archwires made in accordance with the methods. The invention is useful for orthodontics generally. It can be employed with particular advantage in lingual orthodontics, that is, where the orthodontic appliance is attached to the lingual surface of the teeth for aesthetic reasons.

B. Description of Related Art

A widely used method to straighten or align teeth of a patient is to bond brackets onto the teeth and run elastic wires of rectangular cross-sectional shape through the bracket slots. Typically, the brackets are off-the-shelf products. In most cases, they are adapted to a certain tooth (for instance an upper canine), but not to the individual tooth of a specific patient. The adaptation of the bracket to the individual tooth is performed by filling the gap between tooth surface and bracket surface with adhesive to thereby bond the bracket to the tooth such that the bracket slot, when the teeth are moved to a finish position, lies in flat horizontal plane. The driving force for moving the teeth to the desired finish position is provided by the archwire. For lingual brackets, a system has been developed by Thomas Creekmore that has vertical bracket slots. This allows an easier insertion of the wire. The longer side of the wire is therefore oriented vertically. Unitek has marketed this bracket system under the trade name CON-SEAL™.

A computerized approach to orthodontics based on design and manufacture of customized brackets for an individual patient, and design and manufacture of a customized bracket placement jig and archwire, has been proposed in the art. See U.S. Pat. RE 35,169 to Lemchen et al. and U.S. Patents to Andreiko et al., U.S. Pat. Nos. 5,447,432, 5,431,562 and 5,454,717. The system and method of Andreiko et al. is based on mathematical calculations of tooth finish position and desired ideal archform. The method of Andreiko et al. has not been widely adopted, and in fact has had little impact on the treatment of orthodontic patients since it was first proposed in the early 1990s. There are a variety of reasons for this, one of which is that the deterministic approach proposed by Andreiko et al. for calculating tooth finish positions does not take into account unpredictable events during the course of treatment. Furthermore, the proposed methods of Andreiko et al. essentially remove the orthodontist from the picture in terms of treatment planning, and attempt to replace his or her skill and judgment in determining tooth finish positions by empirical calculations of tooth finish positions.

Typically, the wires used in orthodontic treatment today are off-the-shelf products. If they need to be individualized by the orthodontist, the goal is to get along with as few modifications as possible. Therefore, the brackets are designed in a manner that at the end of treatment, when teeth are aligned, the bracket slots are supposed to be located and oriented in a planar manner. This means that a wire that would run passively through the slots, without applying any force, would be planar (flat). This treatment regime is known as "straight wire". It dominates orthodontics worldwide. It is efficient for both manufacturers and the orthodontist. The customized orthodontic appliances proposed by Andreiko et al. call for a flat planar wire, but with the curvature in a horizontal plane customized for the individual and dictated by the shape of the ideal desired archform for the patient.

The so-called straight wire approach that continues to be used in orthodontics today has some noteworthy disadvantages in terms of patient comfort. The need to close the gap between the bracket bonding surface and the tooth surface with adhesive always leads to an increased overall thickness of the appliance. For brackets that are bonded labially, this is acceptable, as labial tooth surfaces are very uniform for different individuals, and the gap to be closed is not significant. However, lingual (inner) surfaces of teeth show a much greater variation among patients. To achieve the goal to orient the bracket in a manner such that the slot is parallel to all other slots when treatment is finished, the thickness of adhesive that is necessary often is in the range of 1 to 2 mm. It is obvious that every fraction of a mm added to appliance thickness significantly increases patient discomfort. Especially with lingual brackets (bracket bonded to the lingual surface of the teeth), articulation problems arise, and the tongue is severely irritated for several weeks after bonding. The tooth surfaces next to these adhesive pads are difficult to clean, thus serving as collecting point for bacteria and causing gingival inflammation. The further the archwire is away from the tooth surface, the more difficult it is to achieve a precise finishing position for each tooth. An error of only 10° in torque (rotation around the wire axis) may well induce a vertical error in tooth position of more than 1 mm.

Another significant disadvantage of thick brackets, especially when bonding lingually, arises when the front teeth are severely crowded (which is often the cause for orthodontic treatment). Since the space is more restricted at the lingual surface due to the curvature of the jaw, not all brackets may be bonded at one session. Rather, the orthodontist has to wait until the crowding has decreased until all brackets may be placed. Crowding also creates problems for labial brackets. Geometrical considerations dictate that this constriction problem becomes worse as the thickness of the bracket/bracket bonding pad/adhesive combination increases.

Another problem in orthodontics is to determine the correct bracket position. At the time of bonding, teeth may be oriented far away from the desired position. So the task to locate the brackets in a manner that a flat planar archwire drives teeth to the correct position requires a lot of experience and visual imagination. The result is that at the end of treatment a lot of time is lost to perform necessary adjustments to either bracket position or wire shape. This problem can be solved by creating an ideal set-up, either virtually using 3D scan data of the dentition or physically by separating a dental model of the dentition into single teeth and setting up the teeth in a wax bed in an ideal position. The brackets can then be placed at this ideal set-up at optimal positions, in a manner that a flat wire running through the bracket slots would drive the teeth exactly into the ideal target. This again may be done virtually in a computer or physically. After this is done, the bracket position has to be transferred on a tooth-by-tooth basis into the maloccluded (initial) situation. Basing on this maloccluded situation, a transfer tray enveloping the brackets can be manufactured, which allows bonding the brackets exactly at the location as defined at the set-up. Such as technique is taught generally in Cohen, U.S. Pat. No. 3,738,005.

The published PCT patent application of OraMetrix, Inc., publication no. WO 01/80761, describes a wire-based approach to orthodontics based on generic brackets and a customized orthodontic archwire. The archwire can have complex twists and bends, and as such is not necessarily a flat planar wire. The entire contents of this document is incorporated by reference herein. This document also describes a scanning system for creating 3D virtual models of a dentition and an interactive, computerized treatment planning system based on the models of the scanned dentition. As part of the treatment planning, virtual brackets are placed on virtual teeth and the teeth moved to a desired position by a human operator exercising clinical judgment. The 3D virtual model of the dentition plus brackets in a malocclused condition is exported to a rapid prototyping device for manufacture of physical model of the dentition plus brackets. A bracket placement tray is molded over the model. Real brackets are placed into the transfer tray in the location of where the virtual brackets were placed. Indirect bonding of the brackets to the teeth occurs via the transfer tray. The system of WO 01/80761 overcomes many of the problems inherent in the Andreiko et al. method.

During the course of treatment, brackets may come off, for instance if the patient bites on hard pieces of food. Obviously, the transfer tray used for initial bonding will not fit any more as teeth have moved. While it is possible to cut the tray (such as described in WO 01/80761) into pieces and use just the one section that is assigned to the bracket that came off, to replace the bracket the reliability of this procedure is limited, as a small piece of elastic material is not adequate to securely position a bracket. It may therefore be required to create a new transfer tray adapted to the current tooth position using a costly lab process.

The methods and applicants presented herein comprise several independent inventive features providing substantial improvements to the prior art. The greatest benefits will be achieved for lingual treatments, but labial treatments will also benefit. While the following summary describes some of the highlights of the invention, the true scope of the invention is reflected in the appended claims.

SUMMARY OF THE INVENTION

In a first aspect, a set of brackets (one or more) is provided in which the bracket has a slot which is oriented with respect to the bracket bonding pad such that the wire runs substantially parallel to the surface of the teeth, i.e., the portion of the tooth surface adjacent to where the bracket receives the archwire, as will be explained in further detail and as shown in the drawings.

In particular, the brackets have a bracket bonding pad for bonding the bracket to the tooth of the patient and a bracket body having a slot for receiving an archwire having either a flat, planar side (e.g., one side of a wire having a rectangular, square, parallelogram or wedge-shaped cross-sectional shape) or alternatively an oval shape. The slots of the brackets are oriented in approximate parallel alignment relative to its respective bracket bonding pad in a manner such that, when the bracket or set of brackets are installed on the teeth of the patient and the archwire is inserted in the slots, the archwire is canted or inclined relative to the occlusal plane (analogous to a banked curve on a high speed racing track). In embodiment in which the archwire has flat surfaces (rectangular, parallelogram, square, wedge shaped, etc), the flat planar side of the archwire is substantially parallel to the surface of the teeth at the location of where the archwire is inserted into the slots, in a canted orientation relative to the occlusal plane. In an embodiment in which the archwire is of an oval configuration, the major axis of the cross-section of the wire is oriented substantially parallel to tooth surface and at a canted orientation relative to the occlusal plane.

For the front teeth, it is desirable to come up with a homogeneous inclination to avoid abrupt changes in inclination (i.e., changes in torque) from slot to slot in order to receive a smooth progression of the wire. In a wire of rectangular or square cross-sectional shape, one of the pairs of parallel opposite sides of the archwire is oriented substantially parallel to the tooth surface. Usually, this will be pair of parallel sides that has the greater width or height. This aspect of the invention enables the overall thickness of brackets to be substantially decreased as compared to prior art techniques, because it does not require a buildup of adhesive to make the slot lie in a horizontal flat plane when the bracket is attached, as found in the straight wire technique. The brackets and archwire design are particularly well suited for use in lingual orthodontics.

This reduction in thickness of the bracket, bracket bonding pad and archwire leads to several significant advantages as compared to prior art systems and satisfaction of a long-felt need in the art for a more satisfactory lingual orthodontic system. These advantages include decreased articulation problems, a pronounced decrease in tongue irritation, a decreased risk of bracket loss, increased positioning control for finishing since the reduced distance between wire and tooth results in more accurate tooth movement to the desired finish position, increased patient comfort, and increased hygiene conditions.

One reason why the basic design of orthodontic wires remains one in which the wires have a flat, planar shape is the ease of industrial manufacturing. To decrease the thickness of an orthodontic bracket, it is much preferable to run the wire parallel to the surface of each individual tooth as provided by this aspect of the invention. The lingual surfaces of front teeth are significantly inclined relative to a vertical axis for most patients. A wire that runs parallel from tooth to tooth in accordance with this aspect of the invention has a "canted" shape in order to take advantage of the parallel nature of the bracket slots. Using standard mass-production procedures, such a wire could not be fabricated, as every patient has a very individual tooth anatomy. Shaping a wire manually to provide the canted shape is extremely challenging. Usage of modern materials for the archwire like shape memory alloys makes this task even more challenging or even impossible by hand. However, in a preferred embodiment of the present invention the required wire geometry is available in electronic format. This wire geometry can be dictated by the three-dimensional location of the bracket slots and/or the brackets, as placed on the teeth in the desired occlusion. This format can be exported to new wire bending robots that have been recently developed that are capable of bending wires in virtually any shape (including canted shapes). For example, it is possible to export digital data reflecting wire geometry to flexible wire bending production devices like the 6-axis-robot described in WO 01/80761, and have the robot bend and twist wires of the canted configuration as described herein. Thus, wires having the canted shape as dictated by the bracket invention are now able to be mass-produced. The presently preferred wire-bending robot is also described in U.S. patent application Ser. No. 09/834,967, filed Apr. 13, 2001, the content of which is also incorporated by reference herein in its entirety.

Thus, in another and related aspect of the invention, a canted archwire is provided. The wire can be of any cross-sectional configuration that has at least one flat planar surface, such as rectangular, or, alternatively, it could be oval in cross-section. The archwire is bent into a configuration during manufacturing to have a shape, in a relaxed, as-manufactured condition, such that the flat planar surface of the archwire (or the major axis of the cross-section of the wire in an oval configuration) is canted relative to an occlusal plane over a substantial arcuate extent. The canting of the archwire corresponds to portions of the archwire that are to be placed in brackets and used for straightening two or more teeth. In an embodiment in which the wire is of rectangular or square cross-section, one of the first and second pairs of parallel sides is oriented substantially parallel to tooth surfaces in the vicinity of where the archwire is to be received by archwire receiving receptacles located on the two or more teeth.

Another aspect of the invention is thus a method of manufacturing an archwire. The method includes the step of defining the location of a set of bracket slots for a set of brackets in three-dimensional space with the aid of a computer. The bracket slots are oriented substantially parallel to the surface of the teeth in the location of where the brackets are to be bonded to the teeth. The method continues with the step of supplying a wire bending robot with information corresponding to the location of the set of bracket slots. This information will be typically in the form of a digital file representing 3D coordinates of the bracket slots. This information can be used by a robot control program to tell a wire bending robot how to bend a wire such that the wire, in a relaxed, as manufactured state, has a shape dictated by the bracket slots. Thus, the method continues with the step of bending an archwire with the wire bending robot having a shape corresponding to the location of the bracket slots, wherein the archwire has a canted configuration such that the archwire is oriented substantially parallel to the tooth surfaces over a substantial arcuate extent. The wire can be bent continuously, or, alternatively, as series of bends separated by straight section corresponding to the bracket slots, as described in more detail in WO 01/80761 and U.S. patent application Ser. No. 09/834,967.

In still another aspect, a bracket is provided with an improved bracket bonding pad that makes the brackets essentially self positioning, that is, it may be uniquely located and positioned on the teeth in the correct location with a positive fit without the use of a jig or other bracket placement mechanism, such as the tray as proposed by Cohen, U.S. Pat. No. 3,738,005, or the jig of the Andreiko et al. patents. In particular, an improvement to a bracket having a bracket bonding pad is provided in which the bracket bonding pad has a tooth contacting surface of three-dimensional area extent conforming substantially exactly to the three-dimensional shape of the tooth where the pad is bonded to the tooth.

In one possible embodiment, the three-dimensional area extent is sufficiently large, and considerably larger than all bracket bonding pads proposed in the prior art, such that the bracket can be readily and uniquely placed by hand and located on the tooth in the correct location due to the substantial area extent corresponding to the three-dimensional surface of the tooth. The bracket is able to be bonded in place on the tooth without the assistance of a bracket placement aid such as a jig. In another possible embodiment, the area extent covers a cusp or a portion of a cusp to enable the bracket to uniquely placed on the tooth.

In another aspect, a bracket is provided with a bracket bonding pad that comprises a thin shell in order to reduce the overall thickness of the bracket as much as possible. The pad includes a tooth-facing surface conforming to the surface of the tooth. In this embodiment the bracket bonding pad has an opposite surface corresponding to the tooth-facing surface which has a three-dimensional surface configuration which also matches the three-dimensional surface of the tooth. In order to create a thin pad on a computer, a preferred method is to create a normal vector of each element of the bracket bonding pad's tooth-facing surface (for instance, a triangle depending on how the surface is represented in the computer). Each surface element is "shifted" in the direction of the normal vector away from the tooth using a pre-defined offset value corresponding to the thickness of the bonding pad. In this way, a thin shell is created, the outside of the shell having substantially the same area extent and three-dimensional surface corresponding to the tooth-facing surface of the bracket bonding pad. Other techniques could be used as well. For example, the bracket bonding pad could have a thinner periphery (e.g., 0.1 mm) and a thicker center portion (e.g., 0.3 mm) adjacent to where the bracket body is attached to the bonding pad. Appropriate software programs can be provided to vary the thickness over the surface of the bracket bonding pad, such as by scaling the normal vector with a variable depending on how close the normal vector is to the edge of the bracket bonding pad.

In yet another aspect of the invention, a method of designing a customized orthodontic bracket for a patient with the aid of a computer is provided. The bracket has a bracket bonding pad. The computer stores a three-dimensional model of the teeth of the patient. The method comprises the steps of determining an area of a tooth at which the bracket bonding pad is to be attached to the tooth; obtaining a three-dimensional shape of a tooth-facing surface of the bracket bonding pad, wherein the three-dimensional shape conforms to the three-dimensional shape of the tooth; and obtaining a three-dimensional shape of a second, opposite surface from the tooth-facing surface of the bracket bonding pad. A library of three-dimensional virtual bracket bodies is stored in the computer or otherwise accessed by the computer. The method continues with the step of obtaining a bracket body from the library and combining the bracket body with the bracket bonding pad to form one virtual three-dimensional object representing a bracket.

In a preferred embodiment, the second, opposite surface has a three-dimensional shape corresponding to the tooth-facing surface of said bracket bonding pad, for example, by performing the "shifting" technique described earlier. The method may also incorporate the optional step of modifying the virtual model of the bracket body. For example, the bracket body may have a portion thereof removed in order to place the slot of the bracket body as close as possible to the bracket bonding pad and delete the portion of the bracket body that would otherwise project into the crown of the tooth. As another example, the modification may include adding auxiliary features to the bracket body such as hooks.

The addition of the bracket body to the bracket bonding pad with the aid of the computer may be performed for a group of teeth at the same time in order to take into account the proximity of adjacent teeth and brackets. Thus, the method may include the step of viewing, with the aid of the computer, a plurality of virtual teeth and virtual bracket bonding pads attached to the teeth, and shifting the location of the bracket body relative to its respective bracket bonding pad. This latter step would be performed for example in order to better position the bracket body on the bonding pad, or in order to avoid a conflict between the bracket body and an adjacent or opposing tooth such as a collision during chewing or during tooth movement.

In yet another aspect of the invention, a method is provided for designing and manufacturing a customized orthodontic bracket. The method includes the step of storing a digital representation of the relevant portion of the patient's dentition in a computer. This could be a digital representation of either the entire dentition, or alternatively only the surfaces of the teeth upon which the brackets are to be bonded. The method continues with the steps of providing access to a library of virtual three-dimensional bracket bodies, such as for example storing the library in the computer, and determining the shape and configuration of bracket bonding pads, with the bracket bonding pads having a tooth-facing surface conforming substantially exactly to corresponding three-dimensional surfaces of the teeth. The method continues with the step of combining the bracket bodies from the library of bracket bodies with the bracket bonding pads to thereby create a set of individual, customized orthodontic brackets. A file representing the customized orthodontic brackets is exported from the computer to a manufacturing system for manufacturing the customized orthodontic brackets. The method continues with the step of manufacturing the customized orthodontic brackets, either using any of a variety of techniques known in the art such as milling, or one of the techniques described in detail herein such as casting.

Still other improvements are provided for manufacturing customized brackets. In one aspect, a method is provided of manufacturing an orthodontic bracket having a bracket body having a slot and a bracket bonding pad, comprising the steps of determining the three-dimensional shape of the orthodontic bracket and manufacturing the bracket from materials having at least two different hardnesses, a first relatively hard material or materials forming the bracket body and a second relatively soft material or materials forming the bracket bonding pad. The strength of the material of the bracket is always a compromise. While the section forming the slot should be as robust as possible to maintain the cross-section of the slot even when the bracket is exposed to high mechanical stress (e.g. by biting on hard objects), the section forming the pad should be softer to ease de-bonding after the treatment is finished. If the pad is soft enough, it can literally be peeled off the tooth surface, using an adequate tool. Depending on the type of the manufacturing process, it is possible to use different alloys to achieve such a configuration. Using centrifugal casting, first, a controlled amount of a hard alloy can be used to form the section that holds the slot, and afterwards a softer alloy is used to fill up the remainder of the bracket (or other way round). Controlling the amount of material needed to form a specific portion of the bracket is possible, since from the 3D models, the volume of each component of the bracket is precisely known. Other manufacturing techniques can be used, such as a laser sintering process, in which different alloy powders are used for the different layers.

In still another aspect, a modular approach to designing customized brackets for an individual patient is provided using a computer. The computer stores a library of virtual bracket bodies, virtual bracket bonding pads, and optionally virtual bracket auxiliary devices such as hooks. The user species or selects a bracket bonding pad and a bracket body for a particular tooth. The two virtual objects are united to form a virtual bracket. The user may be provided with graphics software tools to specify how and where the bracket body and bonding pad are united. Data representing the virtual bracket can be exported to a rapid prototyping process for direct manufacture of the bracket or manufacture of a template or model that is used in a casting process to manufacture the bracket. In one possible embodiment, the bracket bonding pad conforms substantially exactly to the surface of the tooth. Alternatively, the bracket bonding pad could be of a standard configuration.

These and still other principles of the various inventions set forth herein will be discussed in greater detail in conjunction with the appended drawings.

BRIEF DESCRIPTION OF THE DRAWINGS

Presently preferred embodiments of the invention are described below in conjunction with the appended drawing figures, where like reference numerals refer to like elements in the various views, and wherein:

FIG. 3A is a cross section of a tooth with a bracket bonding pad and slot oriented substantially parallel to the tooth surface in accordance with one aspect of a preferred embodiment of the invention.

FIG. 3B is a cross-section of the same tooth shown in FIG. 3A but with a prior art arrangement of a standard Ormco lingual bracket, showing the bracket slot orientation for a horizontal planar archwire that is not canted as shown in FIG. 3A.

FIG. 4 is a perspective view of computer model of two teeth with a bracket bonding pad in accordance with one aspect of the invention perfectly adapted to the tooth surface and covering a substantial area extent of the tooth surface so as to render the bracket manually placeable by the orthodontist in the correct location on the tooth without the use of a jig or other bracket placement device.

FIG. 5 is a view of bite plane devices that may be incorporated onto a bonding pad and bonded on the tooth in order to prevent the upper and lower jaws from closing completely.

FIG. 12 is a view of a set of teeth, partially in cross-section, showing a bracket bonding pad overlying a tooth surface and a bracket body placed on the bracket bonding pad, in an interim step in the performance of a method of designing a customized bracket. The portion of the bracket body projecting into the tooth is eventually removed from the bracket, as shown in FIG. 21.

FIGS. 13A and 13B are perspective views of two representative bracket bodies in which the surfaces thereof are shaped according to the tooth surface, wherein the slots are oriented generally substantially parallel to the surface of the tooth adjacent to where such bracket bodies are bonded to the teeth.

FIGS. 18A and 18B are two views of the pad and bracket body combined as a single virtual object.

DETAILED DESCRIPTION OF PREFERRED EMBODIMENTS

Bracket Slot Parallel to Tooth Surfaces and Canted Archwire

As noted earlier, in the straight wire approach to orthodontics practiced today, the basic design of orthodontic wires in the prior art is a flat, planar shape. All the slots of the brackets, when the teeth are moved to the desired occlusion, lie in a plane. Accordingly, the archwire itself, which is of rectangular cross-section, has a flat, planar configuration. This is also the case for wires to be used with the CONSEAL™ brackets mentioned previously. While the cross-section of the wire is oriented in a vertical manner (the longer side of the wire is vertical), the archwire still forms a plane that is substantially parallel to the occlusal plane and the orientation of the cross-section is maintained along the wire. The primary reason for this phenomenon is the ease of industrial manufacturing of archwires of flat planar configuration. In a first aspect of the invention, we propose a significant departure from flat, planar archwires.

In particular, we have realized that to decrease the thickness of an orthodontic bracket, it is much more preferable to construct the slots of the brackets, and manufacture the archwire, such that the archwire runs essentially parallel to the surface of each individual tooth. In one aspect of the invention, the bracket slots are oriented in a manner such that the wire runs substantially parallel to each tooth surface. What we mean by this is that when a wire, with at least one flat planar surface, is inserted into the bracket slots, the flat planar surface of the archwire is canted or tilted at an oblique angle relative to the occlusal plane. For example, with a wire of rectangular or square cross-sectional shape, one of the pairs of surfaces of the wire is oriented parallel to the tooth surface in a manner inclined relative to the occlusal plane. Similarly, if the wire has an oval cross-section, the major axis of the wire (see FIG. 2B) is oriented substantially parallel to the tooth surface and is inclined at an oblique angle relative to the occlusal plane.

The lingual surfaces of front teeth are significantly inclined. A wire that runs parallel from tooth to tooth particularly in the front teeth would have to have a "canted" shape (analogous to a banked curve on a high speed racing track) relative to the occlusal plane. Using standard mass-production procedures, such a wire could not be fabricated, as every patient has a unique tooth anatomy. Shaping a wire manually is extremely challenging. Usage of preferable materials like shape memory alloy makes this task even more challenging or literally impossible. However, in a preferred embodiment of this invention, the required wire geometry is available in electronic format. It is possible to transport a file representing this wire geometry to a flexible production device like a 6-axis wire bending robot described in WO 01/80761 to bend and twist wires of such a shape.

Figure 1:
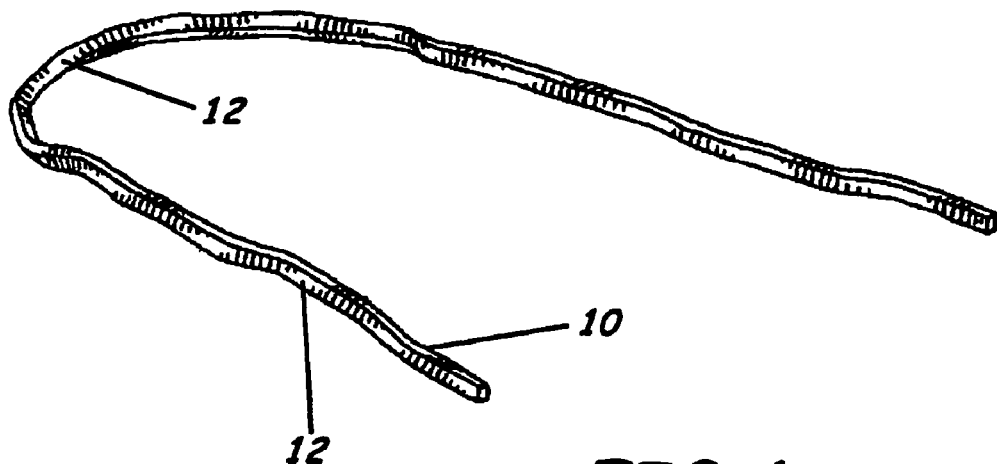
FIG. 1 is a perspective view of a canted archwire in accordance with one aspect of the invention.

FIG. 1 is a perspective view of an archwire 10 with flat sides that is "canted" as provided in this first aspect of the invention. The archwire in the illustrated embodiment is of rectangular cross-section and has two pairs of parallel sides. One of the pairs of parallel sides 12 is of greater height (perpendicular to the axis of the wire) than the other, at least for non-square cross-section wires, and in this embodiment the pair of sides 12 which have the greater height is oriented generally parallel to the tooth surfaces. This can be seen more readily in FIG. 2, which shows the archwire received by three brackets 14 on three of the front teeth 16. The brackets 14 consist of a bracket bonding pad 18 and a bracket body 20 that includes an archwire-receiving slot 22. The slots of the brackets 14 are oriented in approximate parallel alignment relative to its respective bracket bonding pad 18 and associated tooth surface. The arrangement of the bracket slots 22 is in a manner such that, when the brackets 14 are installed on the teeth 16 of the patient and the archwire 10 is inserted in the slots 22, the archwire 10 is canted or inclined relative to an occlusal plane. One of the pairs of parallel opposite sides of the archwire (12 in FIGS. 1 and 2) is oriented substantially parallel to the tooth surface. This aspect of the invention enables the overall thickness of brackets to be substantially decreased as compared to prior art techniques, making the brackets and archwire design particularly well suited for use in lingual orthodontics. The overall thickness of the bracket is also reduced by providing the bracket bonding pad with tooth facing surface and opposite surfaces which conform to the three-dimensional surface of the tooth. Thus, the pad can be constructed as a thin shell (e.g., 0.3 mm in thickness) matching the tooth anatomy.

It is important to note that the canted archwire 10 shown in FIG. 1 is shown "as-manufactured." In other words, the wire has the shape shown in FIG. 1 when the teeth are moved to the finish position and no further forces are imparted onto the teeth. When the wire of FIG. 1 is installed on the teeth in the malocclused condition, the wire will have some other shape, due to the malocclusion, but since the brackets are bonded to the teeth and the bracket slots are oriented generally parallel to the tooth surface, the archwire 10 will still be oriented such that the sides 12 of the archwire are parallel to the tooth surface, thereby providing numerous clinical benefits.

Figure 2:
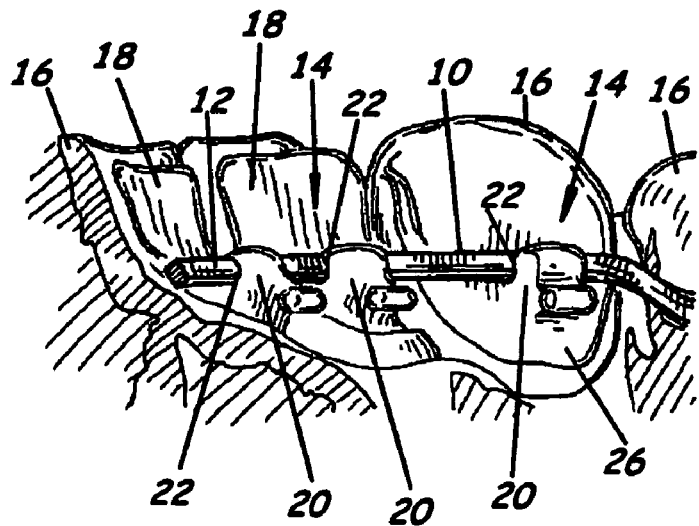
FIG. 2 is an illustration, partially in cross-section, showing a set of teeth, associated brackets and the archwire of FIG. 1.
Figure 2A:
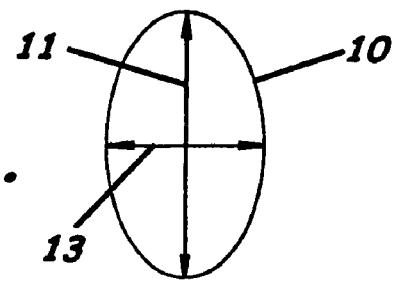
FIG. 2A is a cross-section of an archwire with an oval cross-section that could be used in one possible implementation of this invention.
Figure 2B:
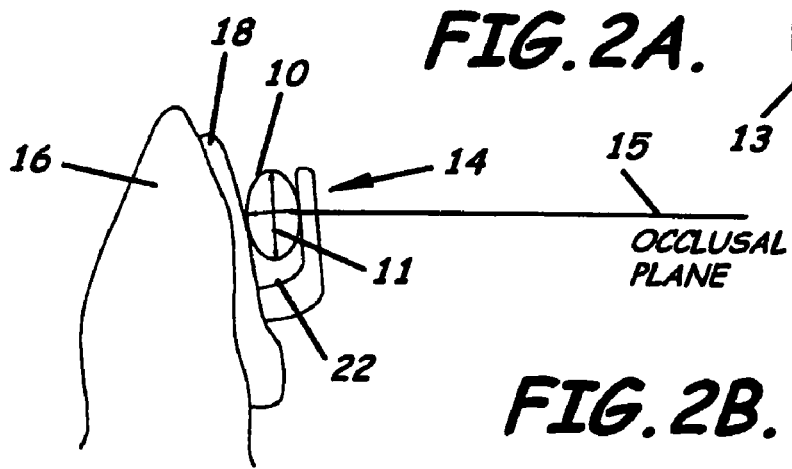
FIG. 2B is a cross-section of the archwire of FIG. 2A placed in a bracket slot with the slot of the bracket oriented substantially parallel to the tooth surface, showing the archwire major axis oriented in a canted configuration with respect to the occlusal plane.

FIG. 2A is a cross-sectional view of an oval archwire 10. The archwire cross-section has an oval configuration with a long or major axis 11 and a minor axis 13. As shown in FIG. 2B, the bracket slot 22 is orientated basically parallel to the tooth 16 surface and the wire 10 is installed in the bracket slot such that the major axis 11 is oriented in a canted or inclined position relative to the occlusal plane 15.

FIGS. 3A and 3B illustrates the advantage of the bracket design and a canted wire: the overall thickness of the bracket can be greatly reduced. FIG. 3A shows the design of a bracket in which the slot 22 is oriented parallel to the tooth surface 16A. FIG. 3B shows a prior art bracket in which the slot 22 is oriented at a substantial angle to the tooth surface at 16A. The bracket slot is parallel to the occlusal plane. In the case of anterior teeth, this results in an inclination between the lingual tooth surface and the bracket slot of approximately 45 degrees. It should be noted here that when we speak of the orientation of the slot, we are referring to the direction of the slot from the opening of the slot 22A to the base of the slot 22B, and not the transverse direction parallel to the axis of the archwire. Thus, the slot in FIG. 3A is oriented parallel to the tooth surface 16A in FIG. 3A. The same orientation is found for all the brackets in FIG. 2. In contrast, the slot in FIG. 3B is oriented at roughly a 45 degree angle to the tooth surface 16A. The slot in the prior art arrangement of FIG. 3B is such that the wire has a flat planar surface that is perpendicular to the occlusal plane, and not canted at an oblique angle as is the case in FIG. 3A and FIG. 2B.

The bracket bonding pad 18 illustrated in FIGS. 2 and 3A conforms exactly to the three-dimensional surface of the tooth and consists of a thin shell. These aspects of the bracket design are described in further detail below.

The reduction in thickness provided by the bracket design of FIGS. 2, 2B and 3A leads to a number of significant improvements as compared to the prior art design shown in FIG. 3B, particularly for lingual orthodontics:

Decreased articulation problems

Decreased tongue irritation

Decreased risk of bracket loss (the flatter the bracket is, the shorter the moment arm is when a patient bites onto the bracket, and the smaller the stress at the adhesive connection)

Increased positioning control for finishing (the smaller the distance between wire and tooth is, the better the tooth "follows" the wire)

Increased patient comfort

Increased hygiene conditions

The orientation of the archwire 10 at the molars may be vertical, as shown in FIG. 1, which results in minimal overall thickness at the molars, or alternatively it could be horizontal. The horizontal orientation would add more thickness (for instance 0.025 inches per side instead of 0.017 inches for a typical wire cross section of 17×25), but the addition is so small that this would certainly be acceptable, if manufacturing or clinical considerations would call for such an orientation. Since a horizontal slot orientation is acceptable for molars and premolars, it would also make sense to mix conventional brackets with brackets according to this invention. For example, the premolars and molar brackets could be conventional brackets, while a set of brackets according to this invention would be supplied for the anterior and canine teeth.

Thus, in one aspect of the invention we have described a bracket, and a set of brackets 14, having slots 22 in which the slots 22 of each of the brackets 14 are oriented in approximate parallel alignment relative to its respective bracket bonding pad 18 in a manner such that, when the set of brackets are installed on the teeth 16 of the patient and the archwire 10 is inserted in the slots, the archwire 10 is canted relative to an occlusal plane to conform to the surface of the teeth at the location of where the archwire 10 is inserted into the slots 22 whereby the overall thickness of the brackets may be decreased.

As shown in FIGS. 2 and 3, the pair 12 of sides of the archwire 10 are oriented substantially parallel to the bracket bonding pad 18 in the region 16A when the archwire 10 is inserted into the slots 22. As shown in FIGS. 2 and 3A, in a preferred embodiment each bracket bonding pad has a three-dimensional tooth facing surface 24 that has a shape to conform exactly to the three-dimensional surface of its respective tooth.

The invention is applicable to both labial brackets and lingual brackets. The brackets in one possible embodiment are essentially self-positioning, as described in more detail below, in that they can be positioned on the tooth in the correct location without the assistance of a bracket placement jig or tray. In the embodiment of FIG. 2, the brackets 14 are lingual brackets and the bracket bonding pad for each of brackets covers a sufficient portion of the lingual surface of the respective tooth so as to be uniquely positioned on the teeth by hand. Note also in FIG. 3A that the bracket bonding pad has a second opposite surface 26 having a three-dimensional shape corresponding to the three-dimensional tooth-facing surface 24 to thereby further decrease the thickness of the bracket.

In one possible embodiment the set of brackets according to this invention may comprise all the brackets for treatment of an arch of the patient. On the other hand, the set of brackets may comprise less than all the brackets for treatment of an arch of the patient and comprise at least one bracket, since the brackets can be mixed with conventional brackets. A set of brackets for placement on the lingual surface of the front teeth of the patient is one representative embodiment. Further, the set of brackets may comprise one subset of brackets for placement on the lower arch and a second subset of brackets for placement on the upper arch.

As noted above, in one possible embodiment the opposite surface of the tooth-facing surface matches the three-dimensional surface of the tooth. The thickness of the bonding pad could be the same across the bonding pad (e.g., 0.3 mm), or alternatively it could vary from say 0.1 mm at the edge of the bonding pad to 0.3 mm in the center. This latter embodiment would provide the required stability on the one hand, and on the other hand promote a peeling off of the pad from the tooth when treatment is completed. Further, the thinner the pad the greater the patient comfort. Presently, casting brackets with a thickness below 0.3 mm is quite challenging, but other manufacturing technologies such as milling or laser sintering could be used instead for manufacturing the pads.

Further design and manufacturing considerations for the brackets of FIGS. 2 and 3A are discussed in detail later on this document.

Self-Positioning Brackets

The "footprint" of the surface 24 of the bracket 14 that is bonded to the tooth ("pad") is a compromise if non-customized pads are used. The smaller it is, naturally the discrepancy between the pad surface and the tooth surface is smaller, and the need to close significant gaps is reduced. On the other hand, the larger it is, the more stable the adhesive joint is, and the smaller the risk of a bracket coming off during the course of treatment.

In another aspect of the invention, we overcome this compromise by shaping the bracket bonding pads 18 (FIGS. 2 and 3A) exactly according to the associated tooth. The shape of the pad's tooth-facing surface 24 is formed as a negative of the tooth 16 surface. This ensures that no conflicts between tooth surface and bracket surface can arise, resulting in the possibility to design each bracket as flat as possible and therefore getting the wire as close to the tooth surface as possible. A very welcome result of this approach is that the bonding surface can be made very large for teeth that show no prominent curvature on the bonding surface, or where the bonding surface can follow the curvature of the cusps. This improves adhesive strength, and by covering a substantial amount of tooth anatomy, the position of the bracket is completely defined by the bracket itself. Even without performing indirect bonding, each bracket is placed exactly at the desired position. If a bracket should still come off, it can easily be repositioned without additional efforts. Because of the bracket bonding pad either covering a substantial area extent of the surface of the tooth or being perfectly adapted to prominent curvatures like cusps, it can be positioned uniquely in the correct location by hand without any jigs or other bracket placement devices. If a bracket comes off during the course of treatment, manual repositioning using the positive fit is highly desirable and indeed possible with these brackets. However, for initial bonding, the use of a tray to simultaneously position multiple brackets may be employed.

The substantial area extent or coverage of the bracket bonding pad depends on the curvature of the tooth surface. In teeth that are rather flat, like the lower anteriors, the area extent may need to be as large as 50 percent or more of the tooth surface for lingual brackets and preferably 70 percent or more for labial brackets. For lingual brackets, this area coverage of the bracket boding pad 18 can be 60 to 75 percent or more. The bracket bonding pads may cover, at least in part, portions of the cusps of the teeth, preferably where such cusps do not make contact with opposing teeth during occlusion or chewing. Where the bracket bonding pad covers the cusp, the manual placement of the bracket and close and unique fit of the bracket to the tooth is further promoted.

FIG. 4 shows an example of lingual brackets 14 in which the bracket bonding pad 18 covers more than 50 percent of the tooth. The bracket bonding pad has a three-dimensional tooth-facing surface 24 (FIG. 3A, not shown in FIG. 4) that is a negative of the surface of the tooth and a second surface 26 which also has the same three-dimensional tooth surface. The manner in which the surfaces 24 and 26 are designed is described in more detail below. Note that the bracket slots need not be parallel to the teeth in this embodiment. Also note that the bracket pad 18 for tooth 16B covers part of the cusp in region 30.

Bracket Design

Brackets according to this appliance system have to be fabricated individually for every patient. Doing this in a lab process would be time consuming and expensive. Designing the bracket slots in the optimal orientation is also challenging. The invention solves this problem by designing the brackets, including the pad geometry in a preferred embodiment, with the help of a computer using virtual three dimensional bracket bonding pads, virtual bracket bodies, and virtual auxiliary devices for brackets such as hooks.

In a preferred embodiment, the bracket design is performed in a workstation that stores a three-dimensional virtual model of the patient's dentition and preferably treatment planning software for moving the teeth in the virtual model to desired finish positions. Such computers are known in the art. See, e.g., WO 01/80761 and Chisti et al., U.S. Pat. Nos. 6,227,850 and 6,217,325, incorporated by reference herein. The design of the brackets in accordance with this invention can be done by a user at an orthodontic clinic, or could be performed at a remotely located manufacturing site.

The pad 18 geometry can be derived directly from digital representations of the patient's teeth so as to produce a bracket bonding pad that conforms substantially exactly to the shape of the surface of the teeth. To achieve this, the shape and size of the bracket pad for each tooth is determined. This may be done manually by using a computer program that allows indicating the desired areas on each tooth model, for instance by drawing virtual lines onto the tooth models or coloring the respective areas. A 3D graphics software program like Magics™, that is widely used to manipulate 3D models that are defined as a set of interconnected triangles (STL-format), allows marking triangles by simply clicking at them with the mouse.

Another option is to use a software algorithm that automatically or semi-automatically calculates an appropriate bracket bonding pad area by analyzing the curvature of the tooth surface and determining a surface that is large enough to cover substantial curvature features to allow for reliable manual positioning of the bracket onto the tooth surface. Such an algorithm could for instance start with a pre-defined pad size. The tooth surface covered by that pad size would form a virtual "knoll" having at least one raised portion relative to surrounding tooth anatomy, as a completely flat tooth surface would not lend itself to unique positioning of a bracket. The volume of the knoll could be calculated provided that the edges of the pad are joined by a continuous surface in any convenient manner. The less curvature the tooth surface presents, the flatter the knoll and the smaller its volume would be. If the volume of the "knoll" does not exceed a pre-defined value, the pad would automatically be enlarged by a predefined value, with the idea that the larger volume would be more likely to include adequate raised tooth features. Again, the volume would be calculated. This loop would be continued until a minimum volume value would be achieved for each pad. Obviously, this is just an exemplary approach for such an automated algorithm. Others could be readily developed from the principles taught herein.

A presently preferred implementation of the bracket pad shape design process is described in further detail below.

Once the pad 18 areas are defined, the shape of this portion of the tooth defines exactly the required shape of tooth-facing portion of the bracket pad. There are several options how to shape the outside portion of the pad. In order to receive a thin pad, the best method is to create the normal vector of each surface element (for instance, a triangle) describing the tooth-facing surface of the pad, and to "shift" each surface element in the direction of the normal vector using a predefined offset value corresponding to the desired thickness of the bracket bonding pad. In this way a thin shell is created, the outside of the shell having the same contour (albeit shifted) as the tooth-facing side. Alternatively, the thickness of the bracket can vary over the surface of the pad with the pad thickness the least at the edges (e.g., 0.1 mm) and greatest (e.g., 0.3 mm) in the center.

Figures 6A, 6B, 6C:
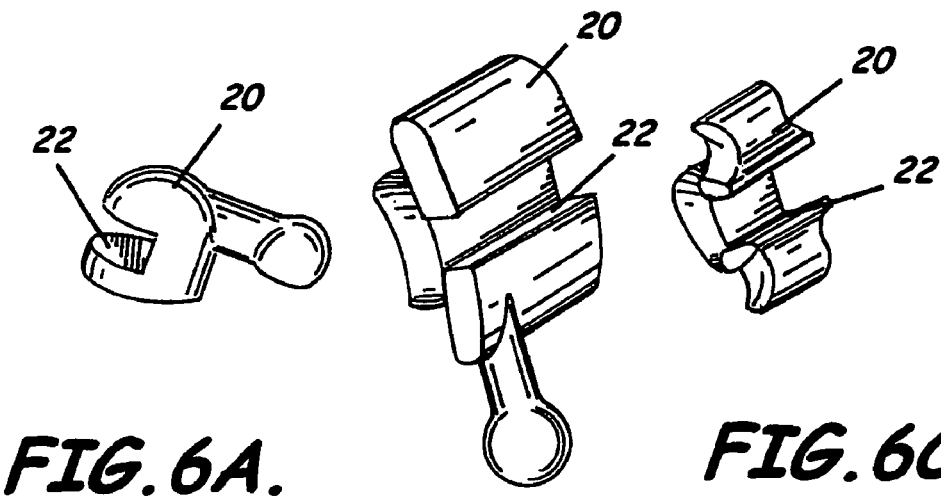
FIGS. 6A, 6B and 6C are standard bracket body shapes that may be used in the design of customized orthodontic brackets. These and other types of bracket bodies are stored as a library of virtual bracket body objects in a computer and used to design customized orthodontic brackets as described in further detail.

The other part of the bracket, the body 20, containing the slot 22 and further features that allow fastening the wire into the slot ("ligating"), may exist as a predefined virtual model in the computer, as the body does not need to be patient specific. Typically, a library of bracket bodies will be created and stored in the computer. FIGS. 6A-6C show perspective views of three-dimensional virtual bracket bodies that are stored in a library of bracket bodies 20 and used for purposes of design of a custom bracket for an individual patient. Alternatively, and equivalently, the library of bracket bodies could be stored elsewhere and accessed remotely. It would be possible to hold a variety of different bodies for different malocclusions and treatment approaches (severe/moderate crowding, extraction/non-extraction etc.). It is also possible to add virtual auxiliary features to the brackets from a library of such features. If, for instance, elastics are required to apply forces along the arch (space closure etc.), hooks may be added. If a patient has a significant overbite and it is desired to prevent him/her from completely closing the jaw, so-called bite planes can be integrated into the bracket. To illustrate this, FIG. 5 shows appliances called bite turbos 32. These appliances 32 are not brackets, but only serve the purpose of providing such a bite plane in order to prevent both jaws from closing completely.

It would even be possible to modify models of bracket bodies according to the requests of an orthodontist. Another advantage is that experiences that are made on certain treatments can almost instantaneously be transformed into the design of the bracket bodies in the library.

After the shape of the bracket bonding pad (including the tooth-facing surface 24 and the opposite surface 26) has been defined, and the user has selected the bracket body 20 that they wish to use for the given bracket bonding pad, the next step is to combine the bracket body 20 with the pad 22. Common Computer Aided Design (CAD) programs have several capabilities to design freeform shapes and to connect existing shapes to each other. One specific method is described in detail below in the Exemplary Embodiment section. Preferably, the user specifies how the bracket body is to be united with the bracket bonding pad to achieve a desired configuration for the customized bracket.

Figure 7:
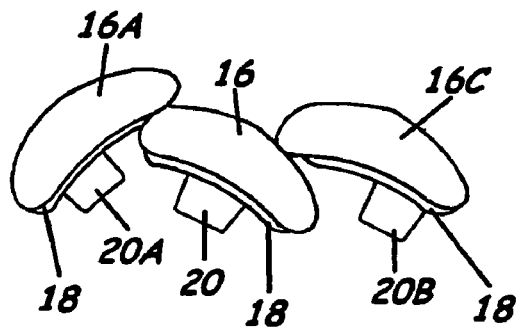
FIG. 7 is a top view of three lower front teeth, showing, in a somewhat simplified manner, how the location of the bracket body on the bracket bonding pad can be adapted to take into consideration the crowding condition of the teeth. The adaptation shown in FIG. 7 is simulated on a computer workstation implementing a bracket design program and allows the user to position the bracket body on the bracket bonding pad in any arbitrary location in order to optimize the placement of the bracket body for the individual patient. The ability to place the bracket body off-set from the center of the pad can be a benefit for labial brackets, e.g., shifting the bracket body in the gingival direction for a lower second bicuspid similar to that provided by the Ormco Mini Diamond™ bracket with gingival offset. This provides a larger bonding area without moving the slot too far to the occlusal portion of the tooth.

Since the exact spatial relation of bracket body and pad can be randomly defined using state of the art 3D graphics software, it is possible to deal for instance with crowded front teeth: The bracket body can be shifted slightly to the left or to the right to avoid conflicts with adjacent teeth and/or brackets, either at the start of treatment or during the course of tooth movement during treatment. This feature is shown in FIG. 7. Note that the position of the bracket body 20A for the left tooth 16A and the bracket body 20B for the right tooth 16C are moved toward one side of the bracket bonding pad 18, so as to avoid collisions between the bracket and the teeth at the start of treatment. Similarly, the bracket body may be moved up or down to avoid a collision with the teeth on the opposing jaw. Alternatively, the user could simply enlarge the pad surface.

As yet another possible embodiment, we contemplate providing the ability of a user to design, with the aid of a computer, a virtual bracket customized for a particular patient. The user is provided with a library containing a plurality of available virtual bracket bonding pads, virtual bracket bodies and optionally virtual auxiliary features. The pad's geometrical shape could be pre-defined (that is, of a given configuration) or could be defined in three dimensions to fit the three-dimensional surface of the patient's teeth exactly as described in detail herein. For example, it would be possible for an orthodontist to order a given pad (for example, pad number 0023 of a list of available pads, with pad 0023 having a predetermined shape), united with a particular bracket body (bracket body number 0011 selected from a list of available bracket body styles), and equipped with hook number 002 for the upper left canine. The user could specify how they wish to unite the bracket bonding bad to the bracket body (such as set forth herein), or they could leave that to the manufacturer. In one possible embodiment, the user specifies the bracket bonding bad, bracket body and auxiliary features, views these components as virtual objects on a workstation or computer, and unites the objects together them to arrive at a unique customized bracket. They then export data representing the bracket to a manufacturing system (such as rapid prototyping system) for direct manufacture of the bracket, or manufacture of a template or model that is used for manufacture of the bracket using a casting process.

Bracket Manufacturing

Once the pad and bracket body have been joined into one 3D object, data representing this object can be exported, for instance in STL format, to allow for direct manufacturing using "rapid prototyping" devices. There are already a wide variety of appropriate rapid prototyping techniques that are well known in the art. They include stereolithography apparatus ("SLA"), laminated object manufacturing, selective laser sintering, fused deposition modeling, solid ground curing, and 3-D ink jet printing. Persons skilled in the art are familiar with these techniques.

In one possible technique, it is possible to use a so-called "wax printer" to fabricate wax models of the brackets. These wax models will then be used as a core in a casting process. They are embedded in cement and then melted. The brackets would be cast in gold or another applicable alloy. It would also be possible to create SLA models and use these as cores in a mold. Other processes, like high-speed milling, could also be used to directly mill the brackets. Processes like laser sintering, where a powdery substance is hardened by a digitally controlled laser beam, are applicable. The powdery substance could be plastic, thus creating cores for a mold, or it could be metal, thus directly fabricating the brackets.

Most rapid prototyping devices shape the objects in layers. This typically causes steps, when a surface is to be modeled is unparallel to the layers. Depending on the thickness of the layers, these steps may hardly be noticeable. However, the surfaces forming the bracket slot 22 should be smooth. One option is to accept steps during the rapid prototyping manufacturing and to mechanically refinish the slots as a last manufacturing step. A better option to avoid steps by orienting the 3D models inside the rapid prototyping device in a manner that the slot is parallel to the layers. In this case, the desired height of the slot must correspond to the layer thickness. In other words, the slot height must be an integer multiple of the layer thickness.

Figure 8:
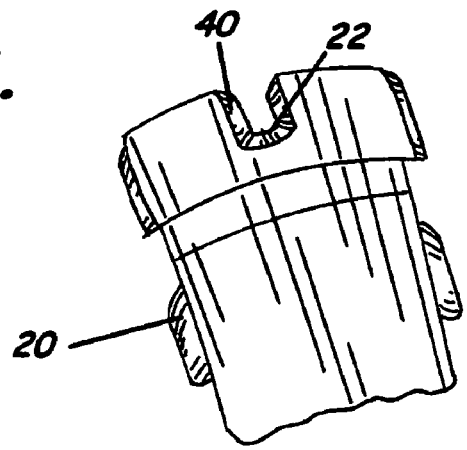
FIG. 8 is an illustration of an Ormco Spirit™ MB ceramic bracket with an inlay for the slot of the bracket.

Another option to receive a smooth slot surface is manufacture the slot larger than the target size and to insert a machined or molded U-shaped inlay into the slot, the inlay thus forming the slot. This is for instance often done at ceramic brackets to reduce friction between wire and slot. This is shown in FIG. 8, in which a U-shaped inlay 40 is placed into the slot 22.

The strength of the material of the bracket 14 is always a compromise. While the section forming the slot 22 should be as robust as possible to maintain the cross-section of the slot even when the bracket is exposed to high mechanical stress (e.g. by biting on hard objects), the section forming the pad 18 should be softer to ease de-bonding after the treatment is finished. If the pad is soft enough, it can literally be peeled off the tooth surface, using an adequate tool. Depending on the type of the manufacturing process, it is possible to use different alloys to achieve such a configuration. Using centrifugal casting, first, a controlled amount of a hard alloy can be used to form the section that holds the slot, and afterwards a softer alloy is used to fill up the remainder of the bracket (or other way round). Controlling the amount of material needed to form a specific portion of the bracket is possible, since from the 3D models of the brackets, the volume of each bracket section is precisely known. If a laser sintering process is used, different alloy powders may be used for the different layers, assuming that the design of the device allows such a procedure.

The modular design generally makes it possible to define the slot height to exactly match the wire cross section. The better the slot is adapted to the wire thickness, the less play the wire has in the slot, and the more precise the tooth location will be at the end of treatment. It would be possible to adapt the slot size of the brackets to a certain lot of wires to be inserted.

The better defined the system bracket/wire is, the less problems will arise during finishing, and the less time will be consumed to deal with such problems. This results in decreased overall treatment time.

Exemplary Embodiment

The process described below is a process that has already been successfully tested. From the comments in the section above, it is obvious that many variations are possible. The reader is directed to FIGS. 2, 3A and 9A-15 in the following discussion. The following discussion is made by way of disclosure of the inventor's best mode known for practicing the invention and is not intended to be limiting in terms of the scope of the invention.

First, a digital three-dimensional representation of the patient's dentition is created or otherwise obtained. One option would be to generate a representation of the malocclusion from a scanning of the malocclusion (either in-vivo or from scanning a model), in which case the digital models of the teeth derived from the digital representation of the dentition would be re-arranged to a desired finishing position with a computer treatment planning program. This process is described at length in WO 01/80761. Another option is to manually create such a finishing position, using a lab process where plaster models are cut into single tooth models, and these tooth models are re-arranged by placing them in a wax bed ("set-up"). A digital representation of the ideal finishing position is then created by scanning this set-up using an industrial laser scanner. This process is also known in the art, see for example the Chisti et al. patents cited earlier.

Once the digital representation of the ideal finishing tooth position has been created, the size and shape of the bracket pad is determined for every tooth. This step, and subsequent steps, have been performed using an off-the-shelf 3D graphics software program known as Magics™, developed by Materialise. Other software programs are of course possible.

Figure 9A:
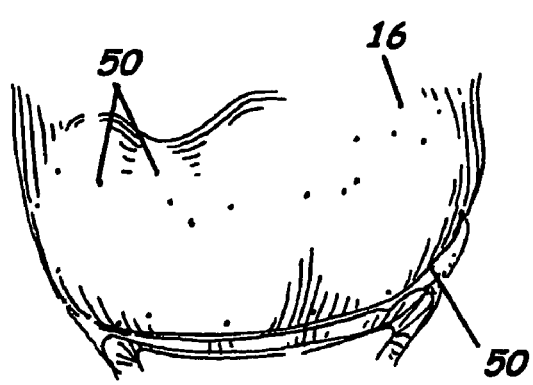
FIG. 9A is an illustration of a virtual tooth displayed on a computer workstation implementing the bracket design features of the present invention, with the user marking the boundary of a bracket bonding pad on the surface of the tooth by placing points on the surface of the tooth.
Figure 9B:
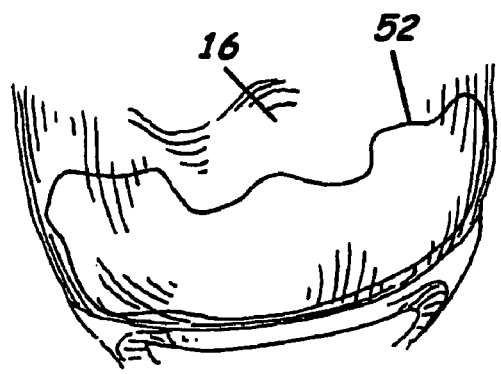
FIG. 9B is an illustration of a curved boundary for the bracket bonding pad, created by joining the points in FIG. 9A with by lines that follow the contour of the tooth surface.
Figure 10:
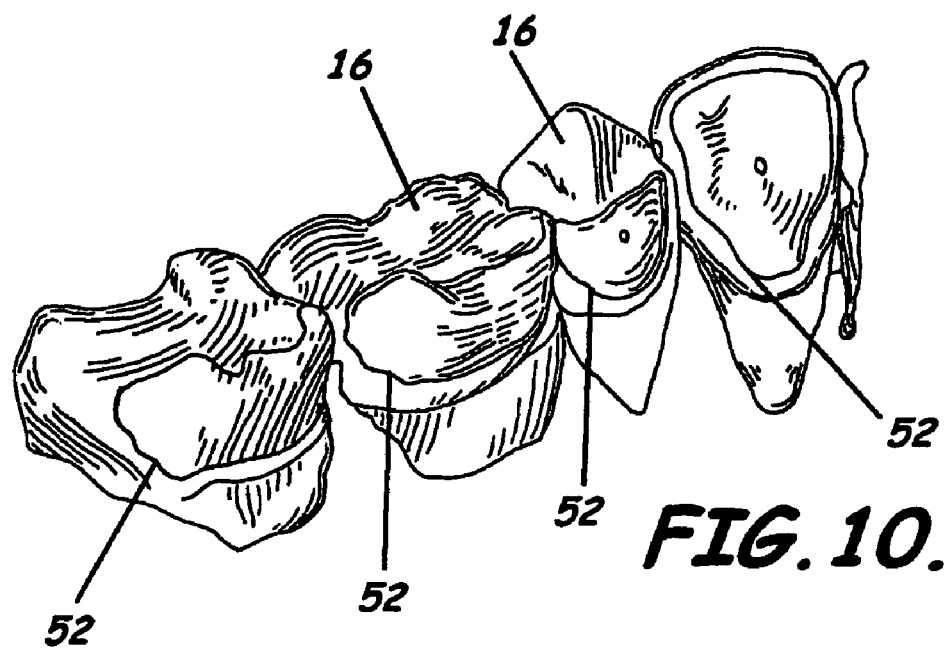
FIG. 10 is an illustration of a set of virtual teeth displayed on a computer workstation implementing the bracket design features of the present invention, showing the pad boundaries that the user has created for a set of teeth. Note that the surface of the teeth covered by the bracket bonding pads may comprise a substantial area extent of the lingual surfaces of the teeth, in this instance approximately 60-75 percent of the lingual surface of the teeth, to assist the user in correctly placing the bracket on the tooth. The area coverage depends on the curvature of the tooth surface, with relatively flat tooth surfaces requiring greater bonding pad area coverage in order for the bracket to be able to be correctly placed without a jig. Where the bracket bonding pad covers part of a cusp of a tooth, the area coverage can be reduced.
Figure 11:
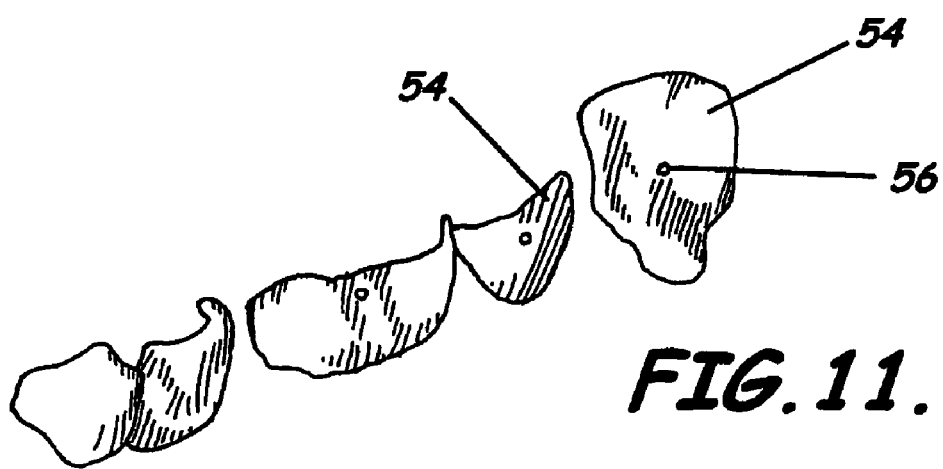
FIG. 11 is an illustration of the tooth surface that is to be covered by the bracket bonding pads. These tooth surfaces are "cut" or separated from the tooth models by performing a separating operation on the workstation, rendering these objects independent three-dimensional surfaces of zero thickness.

For each tooth, the area to be covered by the pad 18 is selected by using the cutting functionality. This is shown in FIGS. 9A and 9B. By clicking at multiple points 50 on the surface of the tooth forming the desired boundary of the bracket bonding pad, this portion of the tooth model is selected for forming the surface at which the bracket bonding pad will be bonded to the tooth. The points 50 are connected by lines 52 automatically. The resulting 3-D polygon is smoothed and the surface enclosed by a line. This surface is turned into an independent surface object in the computer. FIG. 10 shows the process performed for a set of four teeth. The surfaces 54 of the tooth are turned into independent objects as shown in FIG. 11, and consisting of a three-dimensional shell of zero thickness. These surfaces 54 serve as the tooth-facing surfaces of the bracket bonding pad.

Next, the function "Offset Part" in the Magics software is used. Option "Create Thickness" is activated, that uses the normal vectors of the triangles forming the surface 54 to offset the shell 54 and in this way to create a second shell which forms the opposite surface 26 of the bracket bonding pad 18, which is then combined to one continuous surface by closing the gap around the outer edges of the shell. In this way, the three-dimensional shape of the pad 18 is defined. Today's casting technologies will require the pad to have a thickness of typically 0.3 mm.

Next, from the library of virtual bracket body models, the appropriate model of a bracket body is selected for the respective tooth. Typically, one would have different bodies for molars, premolars and front teeth. FIG. 12 shows the placement of a bracket body 20 from the library on a bracket bonding pad 18 at this interim step in the process.

The portion of each bracket body 20, that needs to be merged with the pad 18, is designed to be much longer that needed, so it will stick out on the tooth-facing side of the pad when oriented properly with respect to the tooth. This is the situation shown in FIG. 12. Of course, this is undesirable and the portion projecting inwards from the bracket bonding pad needs to be eliminated.

To make a bracket that is as thin as possible (e.g., for lingual treatments) the goal is obviously to position the slot 22 as close to the pad 18 as possible without creating interference between the pad itself and the slot, or the wire when it runs through the slot.

To remove the portion of the body 20 that is sticking out of the pad towards the interior of the tooth, the original tooth models are re-loaded. The Magics™ software provides "Boolean" operations that include unite functions and subtraction functions. Using these functions, as described below in conjunction with FIG. 16-21, all parts of the bracket body 20 that are inside the tooth model 16 are eliminated. Thus, the bracket body 20 is also shaped precisely according to the tooth surface and is equal to the surface of the pad. FIGS. 13A and 13B show two bracket bodies that have had their surfaces 58 modified so as to conform to the surface of the tooth.

Next, using again a Boolean operation, the pad 18 and the body 20 are united into one three-dimensional virtual object. An object representing the sprue is placed on the bracket (for an embodiment in which the bracket is cast) and also united with the bracket model.

Figure 14:
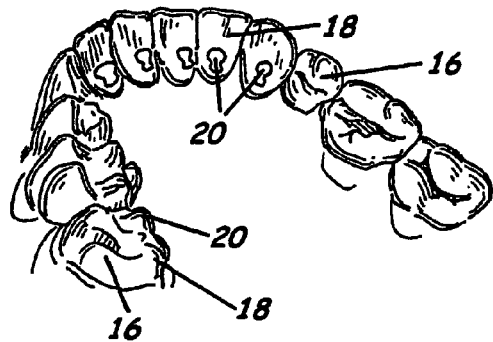
FIG. 14 is perspective view of a digital representation of a set of tooth objects and brackets objects designed in accordance with a preferred embodiment of the invention.

This process is done for each bracket. FIG. 14 shows 3D virtual models of a set of orthodontic brackets for the lingual treatment of the lower arch.

A variation on the above method is as follows. First, the bracket body is retrieved from a library of bracket bodies and placed with respect to the tooth surface in the correct position. Then, the tooth is "subtracted" from the bracket body+tooth object to delete the portion of the bracket body that would otherwise project into the tooth. A bracket bonding pad is created by assigning a thickness to a surface extracted or derived from the tooth surface, using the process described above for surfaces 54. Then, the bracket body, as modified, is united to the bracket bonding pad.

Another possible embodiment is to use bracket bodies that are designed and stored in the computer which are as short as possible. Basically, these virtual bracket bodies would include the slot feature and little or nothing else. The user would position the virtual bracket body adjacent to the virtual bracket bonding pad with a small gap formed between the bracket body and the bracket bonding pad. The bracket designing software includes a feature to generate a surface with a smooth transition between the bonding pad and the bracket body. Software that provides functions to generate a smooth transition between two virtual objects of arbitrary cross-section already exists, one example being a 3D design program sold under the trademark Rhino3D™.

Another alternative and less preferred embodiment for manufacture of customized bracket bonding pads would be to use standard bracket bodies with standard bracket bonding pads, and then bend these pads to the desired three-dimensional configuration using a bending robot. The wire bending robot in WO 01/80761 could be provided with different gripping fingers to grip a bracket and bend the tooth-facing surface of the pad to fit the anatomy of the tooth. The opposite surface of the pad could be shaped by milling. Another embodiment would shape both tooth-facing side and the opposite side by milling.

Another aspect for selecting the appropriate bracket body for a given tooth is the extent of the malorientation of the tooth. For instance, a tooth that is significantly angulated should be equipped with a wide bracket bonding pad to provide satisfactory control, whereas a tooth that does not require a change in angulation could receive a very narrow bracket bonding pad since no angulation moment needs to be incorporated into the tooth.

Thus, from the foregoing discussion, it will be appreciated that a variety of methods for designing and manufacturing the brackets of the present invention are contemplated. Still others may be selected by persons skilled in the art. The process of designing brackets occurs for all the required teeth in the arch and the process is performed for the opposing arch if desired.

The 3D models of the finished customized brackets in STL format are exported and fed into a wax printer. Such a wax printer is designed similar to an inkjet printer and builds up the object in a large number of thin layers. The bottom layer is "printed" first: a fine jet blows liquid wax onto a base plate. The portions that are part of the object to be fabricated are printed using a wax with a high melting temperature. The remaining portions are filled with a wax of a low melting temperature. Then, the surface of the first layer is milled to receive a planar layer of a precisely defined thickness. Afterwards, all further layers are applied in the same manner. After this is complete, the low-melting portions are removed by exposing them to a heated solvent.

The wax models of all brackets are then embedded in cement, making sure that the sprue is not completely covered. After the cement is hardened, the mold is heated, so that the wax cores are removed, and cavities are created. A gold-based alloy is cast into the mold. Then the mold is destroyed, and the brackets are ready for use after removal of the sprue.

The resulting customized brackets could be bonded one by one, but it is more efficient to place them onto a plaster model of the malocclusion, fixing them with a drop of liquid wax or a water soluble adhesive, and to overmold the complete set with silicone, thus creating a bracket transfer tray.

Obviously, a transfer tray according to OraMetrix's method of using an SLA representation of dentition plus brackets described in WO 01/80761, could also be used.

After the process of designing brackets is done for the entire arch, the position of the bracket slots for the entire arch is stored as a file and exported to a wire bending robot for bending of an archwire. To manufacture the wires, a six-axis-robot as described in WO 01/80761 is appropriate and a preferred embodiment. Since the location and orientation of each bracket is known and therefore the location and orientation of each slot, it is possible to generate robot control files, containing the spatial information on each slot, and to use these control files to bend a wire having the configuration shown in FIG. 1.

The Magics™ software program allows the user to export co-ordinate systems of individual objects in a proprietary file format. These are ASCII files with the extension UCS. Such a file can be imported into conversion software and turned into the CNA format used by the robot in WO 01/80761, which holds transformation matrices in binary format. Obviously, if the complete process of virtual set-up and virtual bracket design and placement would be performed within the native software of the wire bending system, such a conversion would not be required, as CNA files would be directly generated.

Figure 15A:
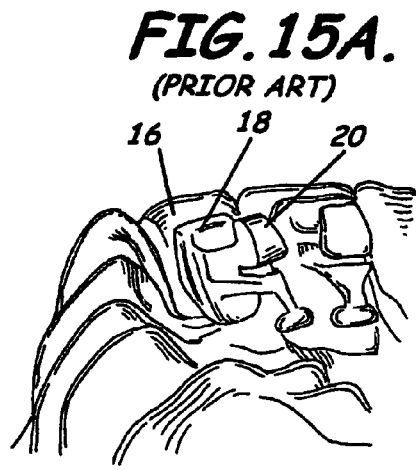
FIG. 15A is an illustration of a prior art lingual bracket arrangement.
Figure 15B:
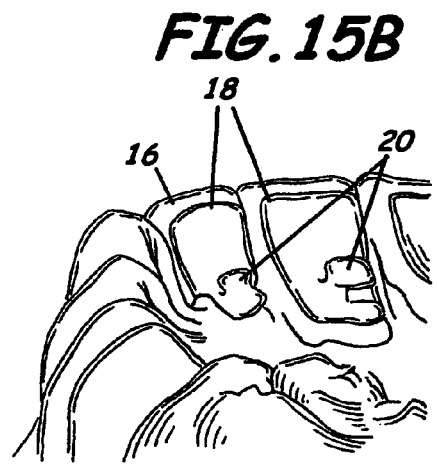
FIG. 15B is an illustration of the same teeth but with customized brackets in accordance with the bracket design features of this invention. A comparison of FIGS. 15A and 15B shows the pronounced decrease in bracket thickness in FIG. 15B.

FIG. 15A shows prior art lingual brackets in which the straight wire approach is used. Note the large size of the brackets. This results in much discomfort for the patient, articulation problems, and other problems as discussed previously. Compare FIG. 15A to FIG. 15B, a set of brackets provided in accordance with the teachings of this invention. The brackets are of a much reduced thickness. The advantages of the bracket and wire system of FIG. 15B has been set forth above.

Figure 16:
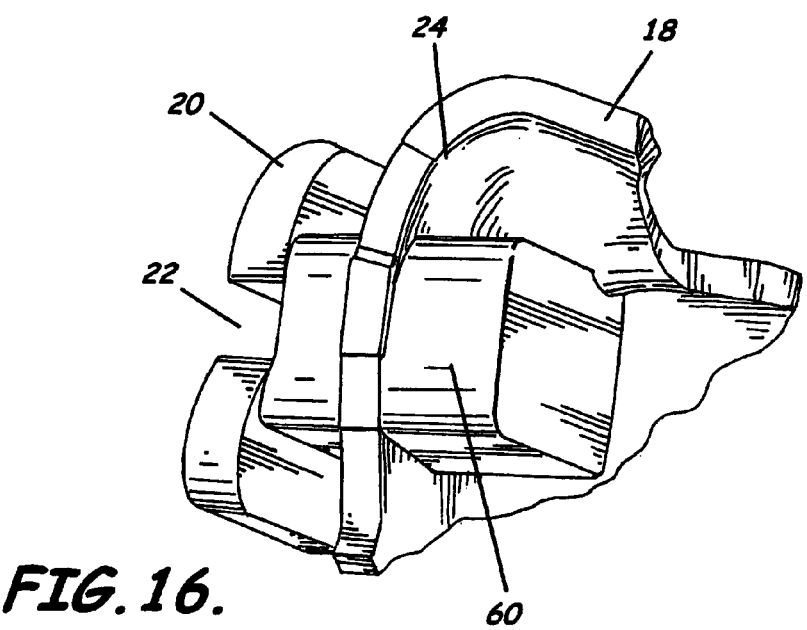
FIG. 16 shows the combination of a virtual bracket body and virtual bracket bonding pad during an intermediate step in the design of a customized orthodontic bracket, in which the pad and bracket body are two independent three-dimensional virtual objects which can be moved relative to each other.

Referring now to FIGS. 16-21, a presently preferred process of merging the bracket body 20 with the bracket bonding pad 78 in the computer will now be described. FIG. 16 shows the combination of a virtual bracket body 20 and virtual bracket bonding pad 18 during an intermediate step in the design of a customized orthodontic bracket, in which the pad 18 and bracket body 20 are two independent three-dimensional virtual objects which can be moved relative to each other. In the situation shown in FIG. 16, the slot 22 is positioned relative to the pad 18 where the user wants it, but the portion 60 of the bracket body is projecting beyond the tooth contact surface 24 of the pad, which is an undesirable result.

Figure 17:
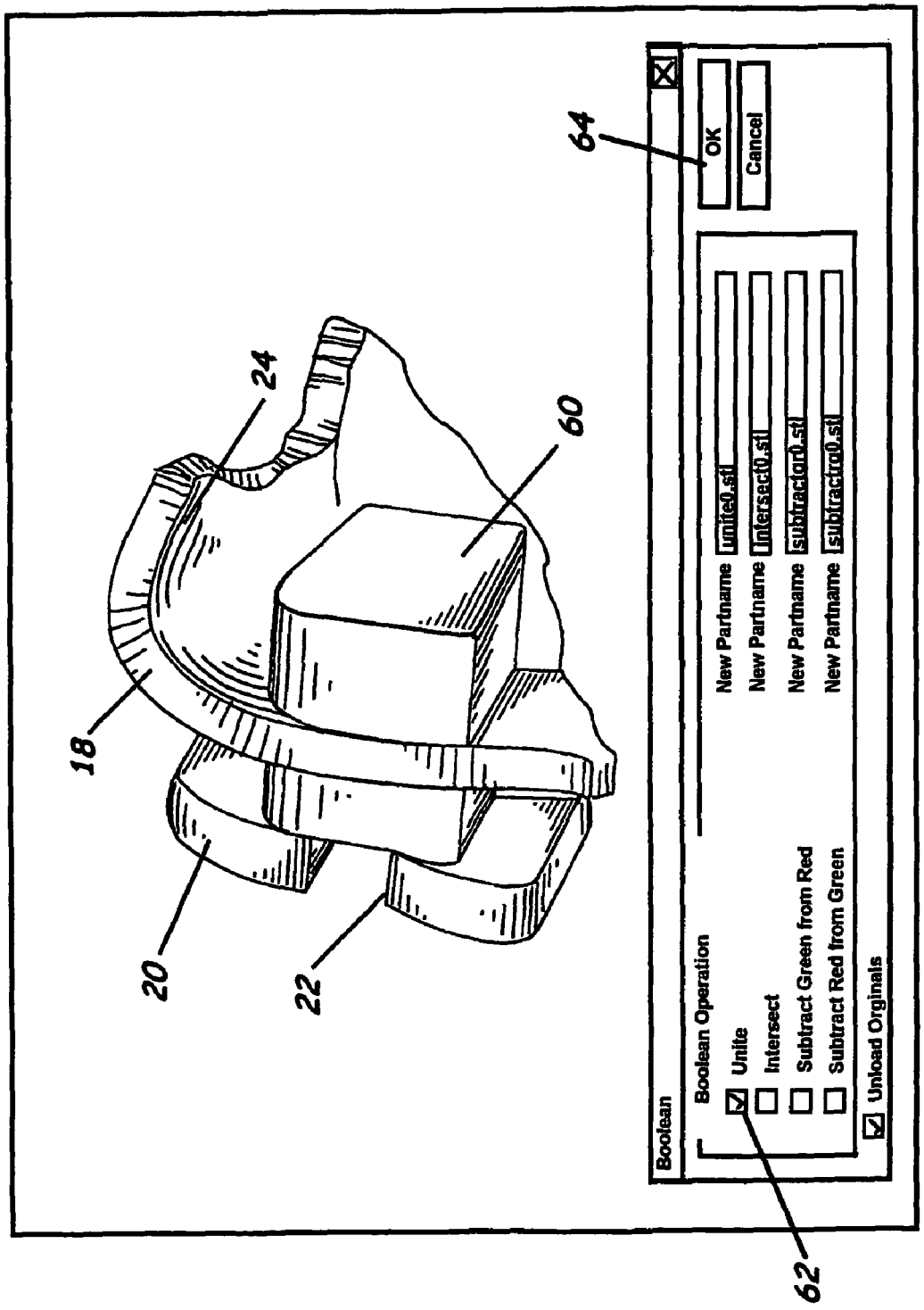
FIG. 17 shows the screen of a computer workstation implementing the bracket design features described herein, in which the user is uniting the pad and bracket body of FIG. 16 into a single virtual object.

FIG. 17 shows the screen of a computer workstation implementing the bracket design features described herein, in which the user is uniting the pad and bracket body of FIG. 16 into a single virtual object. The pad 18 is represented as a red object on the workstation user interface and the bracket body is a green object. The Magics™ software provides a unite icon, indicated at 62. When the user clicks OK at 64, the two objects 20 and 18 are united into one virtual 3D object. FIGS.

18A and 18B are two views of the pad and bracket body combined as a single virtual object.

Figure 19:
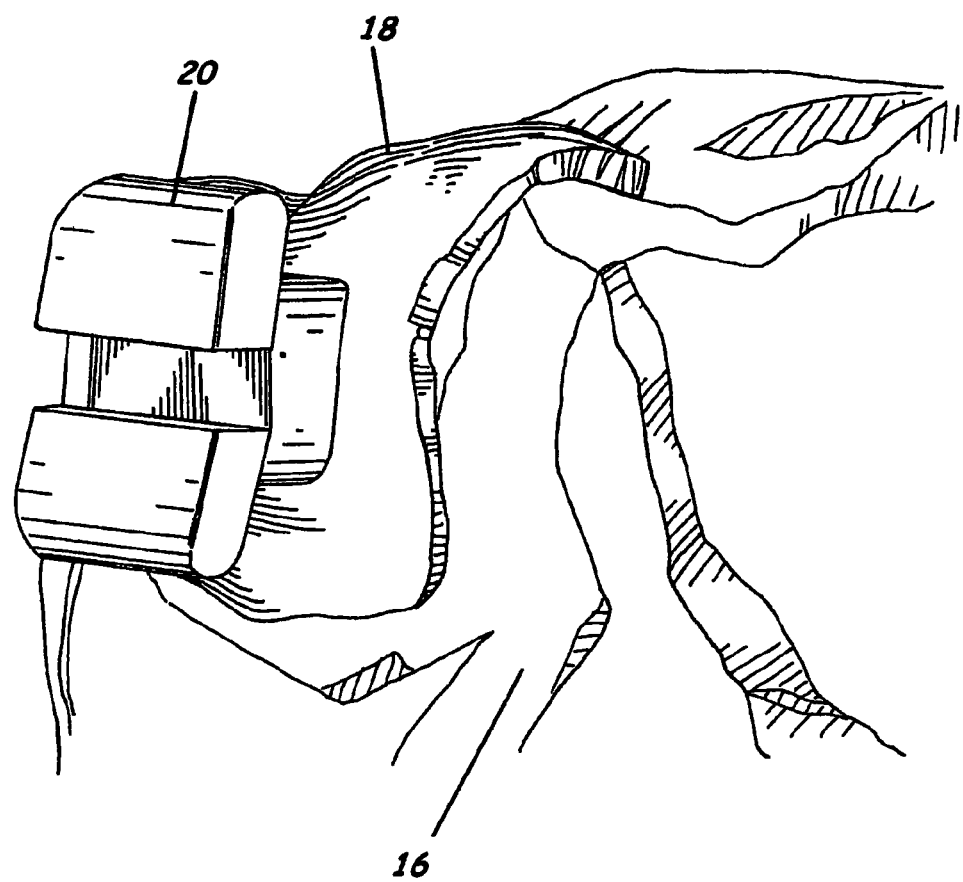
FIG. 19 shows the pad and bracket body of FIGS. 18A and 18B placed on a virtual tooth.

Next, the tooth object is recalled and the bracket body/pad object is superimposed on the tooth. FIG. 19 shows the pad 18 and bracket body 20 of FIGS. 18A and 18B placed on a virtual tooth 16.

Figure 20:
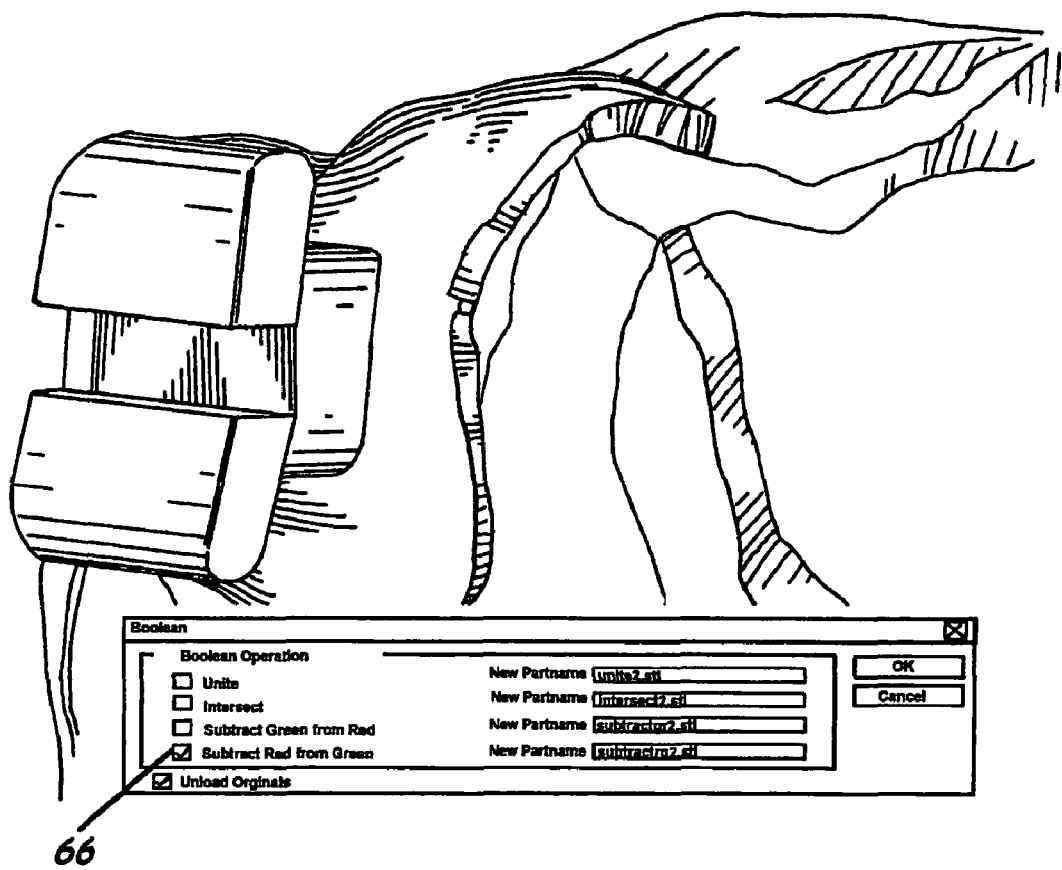
FIG. 20 shows the screen of a computer workstation performing a subtraction process to subtract the tooth object represented in red on the workstation from the bracket bonding pad/bracket body object rendered in green on the workstation. This step is needed to remove the portion of the bracket body that would otherwise project inside the tooth.

Now, the portion 60 (FIG. 18) needs to be removed from the bracket. FIG. 20 shows the screen of a computer workstation performing a subtraction process to subtract the tooth object 16 represented in red on the workstation from the bracket bonding pad/bracket body 18/20 object, rendered in green on the workstation. This step is needed to remove the portion of the bracket body 60 that would otherwise project inside the tooth. The user activates the icon 66 indicating subtraction of the red (tooth) from the green (bracket pad/body) and clicks OK.

Figure 21A:
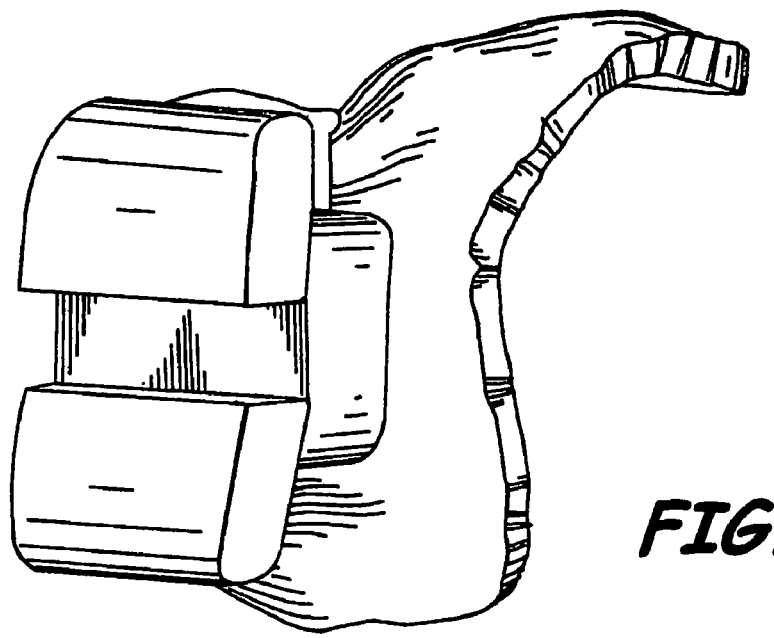
FIGS. 21A and 21B are two views of the bracket pad/bracket body object after the subtraction operation of FIG. 20 has been performed. By comparing FIG. 17 with FIG. 21B, it will be seen that the portion of the bracket body that would have otherwise projected within the tooth has been deleted from the bracket pad/bracket body object.
Figure 21B:
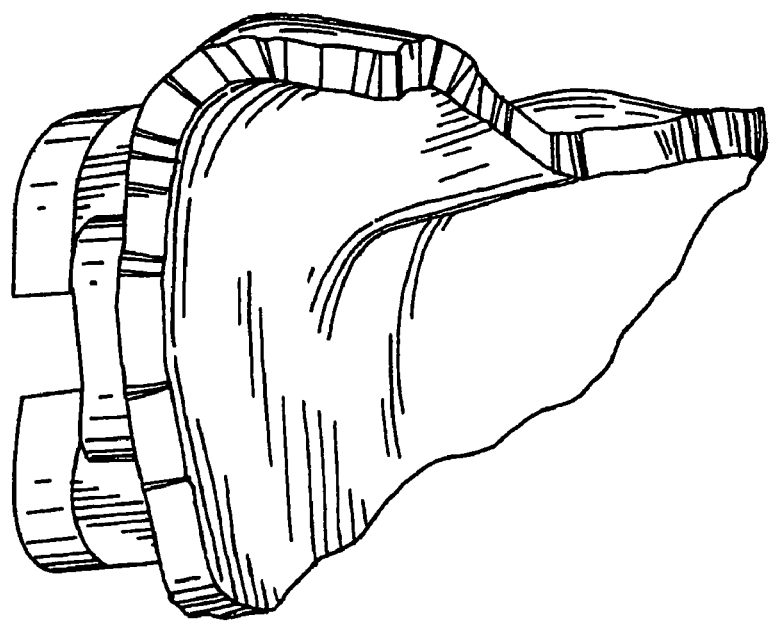

FIGS. 21A and 21B are two views of the bracket pad/bracket body object after the subtraction operation of FIG. 20 has been performed. By comparing FIG. 17 with FIG. 22, it will be seen that the portion 60 of the bracket body that would have otherwise projected within the tooth has been deleted from the bracket pad/bracket body object and the tooth-facing surface 24 conforms exactly to the surface of the tooth.

As noted above, it would be possible to space a virtual bracket body from a virtual bracket bonding pad in a desired spatial relationship with respect to each other and fill in the volume of space between the two objects with a suitable graphics tool, such as the Rhino3D program, to thereby unite the bracket body with the bracket bonding pad. Alternatively, the bracket body could be fit exactly to the bracket bonding pad using 3D graphics software tools without requiring any portion of the bracket body to be removed. In this situation, the two virtual objects intersect in a manner that the bracket body would penetrate the pad only (e.g., a depth of intersection of the bracket body and the bracket bonding pad of say 0.1 mm). Alternatively, the two objects could be united as described above and the portion that would otherwise project inside the tooth is removed as shown in FIGS. 16-21.

The archwires to be used with this invention can be of any suitable archwire material known in the art or later developed. It has been found that relatively soft, heat treatable alloys are particularly suitable. It has been discovered that such wires are also ideal for bending with a wire bending robot. One such alloy which is a preferred material for the instant inventions is a cobalt chromium alloy sold under the trademark BLUE ELGILOY™, available from Rocky Mountain Orthodontics. This particular wire material has a composition of 40% cobalt, 20% chromium, 15% nickel, 7% molybdenum, 2% manganese, 0.15% carbon, balance iron. A similar alloy is available from Ormco, sold under the trademark AZURLOY™. These materials are particularly well suited for the six-axis wire bending robot with heated gripper fingers described in WO 01/80761. The cobalt chromium alloys are rather soft, which is particularly desirable for lingual treatment. Also, significantly, they require very little overbending to achieve the desired bend in the wire, which is particularly advantageous from a wire bending point of view since overbending of wires to achieve the desired shape of the wire after bending is complete is a difficult process to control exactly.

The cobalt chromium wire are preferably heat treated after bending to increase the strength of the wire. The heat treatment can be provided by the robot gripping fingers using resistive heating techniques, immediately after each section of the wire is bent, using the techniques described in WO 01/80761. Alternatively, the heat treatment can be performed after bending the entire wire by placing the wire in an oven, or, alternatively the wire can be placed in a wire heating apparatus described in U.S. Pat. No. 6,214,285. The temperature for heat treatment is approximately 500 degrees F. The purpose of heat treatment of the wire here, to give the wire additional strength, is different from the purpose of heat treatment of NiTi and other shape memory wires described in WO 01/80761. The heat treatment of NiTi wires is needed to have the material take on the configuration of the wire as bent by the robot, whereas here the cobalt chromium wire will take the bend even without heat treatment, as the heat treatment here is for the purpose of increasing strength of the wire.

These relatively soft wires, particularly the cobalt chromium alloys, which require very little overbending, are especially suited for lingual orthodontic brackets and canted archwires as described herein. In one possible aspect of the invention we provide a method of forming an archwire with a wire bending robot in which the wire comprises a cobalt chromium alloy that is subsequently heat treated, for example by the wire gripping apparatus of the wire bending robot as described in WO 01/80761. In another aspect a method for bending and heat treating an archwire is provided, comprising the steps of supplying the archwire to a wire bending robot, bending the archwire with the wire bending robot to have a predetermined configuration for a particular orthodontic patient, and heat treating the archwire while said wire is held by the wire bending robot. Preferably, the archwire comprises a cobalt chromium wire, but other alloys that require heat treatment after bending could be used. The step of bending and heat treating could be provided by bending the archwire is bent in a series of bends and heating the wire after performing each of the bends in the series of bends.

While presently preferred embodiments have been described with particularity, variation from the preferred and alternative embodiments is of course possible without departure from the spirit and scope of the invention. For example, the designing of the brackets with the aid of a computer has been described using the Magics™ software program in which surface elements of the bracket bonding pad, tooth and bracket body are represented as triangles. However, there are other acceptable mathematical techniques for representing arbitrary three-dimensional shapes in a computer, including volumetric descriptions (IGES format), and Nonuniform Rational B Splines (NURB), that could be used. While representation of surface elements using triangles (SLA format) works well in this invention, software using NURBs such as QuickDraw3D™ could be used. NURB software is becoming more and more prevalent, since it offers a way of representing arbitrary shapes while maintaining a high degree of mathematical exactness and resolution independence, and it can represent complex shapes with remarkably little data. The methods and software used in the preferred embodiment for designing the brackets in accordance with the invention represent one of several possible techniques and the scope of the invention is not limited to the disclosed methods.

As another example, the manufacturing techniques that are used for manufacture of the brackets is not critical and can vary from the disclosed techniques.

The reference herein to archwires with a rectangular, square or similar cross-section is considered to encompass archwires that basically have this cross-sectional form but have slightly rounded corners and as such are not exactly of rectangular or square cross-section. Similarly, the reference to the appended claims of an archwire having a flat planar side is intended to cover an archwire that basically has a flat planar side, notwithstanding a rounded of the corner from one face of the wire to another face.

This true spirit and scope of the invention will be understood by reference to the appended claims.

We claim:

1. A method of designing and manufacturing a custom orthodontic lingual bracket including a tooth-facing surface and a bracket body, the method comprising the steps of:
   storing a digital representation of portions of a dentition of a specific patient in a computer memory;
   determining a shape of a tooth-facing surface of a custom shaped virtual bracket bonding object, the shape of the tooth-facing surface conforming substantially to corresponding three-dimensional surfaces of a lingual portion of a tooth of the specific patient;
   forming the custom shaped virtual bracket bonding object having tooth-facing surface conforming substantially to corresponding three-dimensional surfaces of the lingual portion of the tooth;
   graphically displaying the custom shaped virtual bracket bonding object;
   receiving a three-dimensional virtual description of a non-custom bracket feature from the computer memory, the non-custom bracket feature comprising a virtual bracket;
   graphically displaying the received three-dimensional virtual description of a non-custom bracket feature;
   graphically designing a custom orthodontic lingual bracket using a computer, the designing including the step of virtually incorporating the graphically displayed custom shaped virtual bracket bonding object and the graphically displayed three-dimensional virtual description of a non-custom bracket feature into a combined three-dimensional virtual object describing the custom orthodontic lingual bracket;
   exporting digital data representing the virtual description of the designed custom orthodontic lingual bracket from the computer to a manufacturing system for manufacturing the custom orthodontic lingual bracket; and
   manufacturing the custom orthodontic lingual bracket to include shaping the tooth-facing surface and the bracket body of the custom orthodontic lingual bracket responsive to the digital data.

2. A method as defined in claim 1,
   wherein the step of forming the custom shaped virtual bracket bonding object includes forming the tooth-facing surface as a negative of the shave of a substantial portion of the tooth surface; and
   wherein the step of exporting digital data representing the custom orthodontic lingual bracket includes exporting digital data representing the combined three-dimensional virtual object.

3. A method as defined in claim 1, wherein the combined three-dimensional virtual object describing the custom orthodontic lingual bracket comprises a Boolean combination of the graphically displayed custom shaped virtual bracket bonding object and the graphically displayed three-dimensional virtual description of a non-custom bracket feature.

4. A method of designing and manufacturing a custom orthodontic lingual bracket including a tooth facing surface and a bracket body, the method comprising the steps of:
   storing a digital representation of portions of a dentition for a specific patient in a computer memory;
   determining a shape of a lingual portion of a tooth of the specific patient to thereby form and graphically display a custom shaped virtual bracket bonding object having a tooth-facing surface conforming substantially to corresponding three-dimensional surfaces of the lingual portion of the tooth;
   forming the custom shaped virtual bracket bonding object to include forming the tooth-facing surface as a negative of the shape of a substantial portion of a tooth surface of the lingual portion of the tooth of the specific patient;
   graphically displaying the custom shaped virtual bracket bonding object;
   receiving a graphically displayed three-dimensional virtual description of a non-custom bracket feature from the computer memory, the non-custom bracket feature including a virtual bracket body;
   graphically displaying the received three-dimensional virtual description of a non-custom bracket feature;
   graphically designing a custom orthodontic lingual bracket using a computer, the designing including the step of virtually incorporating the graphically displayed custom shaped virtual bracket bonding object and the graphically displayed three-dimensional virtual description of a non-custom bracket feature into a combined three-dimensional virtual object describing the custom orthodontic lingual bracket;
   exporting digital data representing the designed custom orthodontic lingual bracket from the computer to a manufacturing system for manufacturing the custom orthodontic lingual bracket; and
   manufacturing the custom orthodontic lingual bracket to include shaping the tooth-facing surface and the bracket body of the custom orthodontic lingual bracket responsive to the digital data.

5. A method as defined in claim 4,
   wherein the step of exporting digital data representing the custom orthodontic lingual bracket includes exporting digital data representing the combined three-dimensional virtual object.

6. A method as defined in claim 4, wherein the combined three-dimensional virtual object describing the custom orthodontic lingual bracket comprises a Boolean combination of the graphically displayed custom shaped virtual bracket bonding object and the graphically displayed three-dimensional virtual description of a non-custom bracket feature.

7. A method of designing for custom-shaping a custom orthodontic lingual bracket including a tooth-facing surface and a bracket body for an individual patient with the aid of a computer having access to a library of three-dimensional virtual descriptions of bracket features, the method comprising the steps of:
   determining a three-dimensional shape of a tooth-facing surface of a first graphically displayed three-dimensional virtual orthodontic bracket object, the tooth-facing surface conforming substantially to corresponding three-dimensional surfaces of a lingual portion of a tooth of a specific patient;
   receiving from the library at least one graphically displayed three-dimensional virtual representation of a bracket feature for the first graphically displayed three-dimensional virtual orthodontic bracket object; and
   graphically updating the graphically displayed first graphically displayed three-dimensional virtual orthodontic bracket object by adding the at least one graphically displayed three-dimensional virtual representation of the bracket feature, the graphically updated first graphically displayed three-dimensional virtual orthodontic bracket object defining a second three-dimensional virtual orthodontic bracket object to be used for shaping of the tooth-facing surface and of the bracket body of the custom orthodontic lingual bracket.

8. A method as defined in claim 7,
   wherein the at least one three-dimensional virtual representation of a bracket feature comprises an archwire slot adapted to receive an archwire;

wherein the step of graphically updating the first three-dimensional virtual orthodontic bracket object includes graphically virtually orienting the virtual representation of the archwire slot relative to the tooth-facing surface of the first three-dimensional virtual orthodontic bracket object; and wherein the method further comprises the step of shaping the custom orthodontic lingual bracket according to the second three-dimensional virtual orthodontic bracket object, the step of shaping comprising shaping of the tooth-facing surface and shaping of the bracket body of the custom orthodontic lingual bracket.

9. A method as defined in claim 7,
wherein the at least one three-dimensional virtual representation of a feature comprises a virtual hook; and
wherein the step of graphically updating the first three-dimensional virtual orthodontic bracket object includes graphically virtually orienting the virtual representation of the hook relative to the tooth-facing surface.

10. A method as defined in claim 7, wherein the first graphically displayed three-dimensional virtual orthodontic bracket object comprises a bonding pad, and wherein the at least one three-dimensional virtual representation of a feature comprises an archwire slot.

11. A method as defined in claim 7, wherein the first graphically displayed three-dimensional virtual orthodontic bracket object comprises a bonding pad having a greater thickness in medial portions than in peripheral portions thereof.

12. A method of designing for custom-shaping a custom orthodontic lingual bracket including a three-dimensional tooth-facing bonding surface and a bracket body for an individual patient with the aid of a computer having access to a library of three-dimensional virtual descriptions of bracket features, the method comprising the steps of:

determining a three-dimensional shape of a lingual tooth-facing surface of a first graphically displayed three-dimensional virtual orthodontic bracket object responsive to data describing a three-dimensional shape of a corresponding lingual portion of a tooth surface of a specific tooth of a specific patient, the three-dimensional shape of the lingual tooth-facing surface of the first graphically displayed three-dimensional bracket object substantially matching the three-dimensional shape of the corresponding lingual portion of the tooth surface of the specific tooth to conform substantially thereto;

receiving from the library at least one graphically displayed three-dimensional virtual representation of a feature for the first graphically displayed three-dimensional virtual orthodontic bracket object; and updating the first graphically displayed three-dimensional virtual orthodontic bracket object by subtracting the at least one graphically displayed three-dimensional virtual representation of the feature from the graphically displayed three-dimensional virtual orthodontic bracket object, the updated first graphically displayed three-dimensional virtual orthodontic bracket object defining a second graphically displayed three-dimensional virtual orthodontic bracket object configured to be used for shaping of the three-dimensional tooth-facing bonding surface and of the bracket body of the custom orthodontic lingual bracket.

13. A method as defined in claim 12,
wherein the at least one three-dimensional virtual representation of a feature comprises an archwire slot for receiving an archwire;
wherein the step of updating the first graphically displayed three-dimensional virtual orthodontic bracket object includes orienting the virtual representation of the archwire slot relative to the tooth-facing surface; and
wherein the method further comprises the step of shaping the custom orthodontic lingual bracket according to the second three-dimensional virtual orthodontic bracket object, the step of shaping comprising shaping of the three-dimensional bonding surface and of the bracket body of the custom orthodontic lingual bracket.

14. A method as defined in claim 13, wherein the graphically displayed first three-dimensional virtual orthodontic bracket object includes a bonding pad having an increased thickness adjacent the slot.

15. A method as defined in claim 12, wherein the first graphically displayed three-dimensional virtual orthodontic bracket object comprises a bonding pad, and wherein the at least one three-dimensional virtual representation of a feature comprises an archwire slot.

16. A method as defined in claim 12, wherein the first graphically displayed three-dimensional virtual orthodontic bracket object comprises a bonding pad having a greater thickness in medial portions than in peripheral portions thereof.

17. A method of designing for custom-shaping a custom lingual orthodontic bracket including a three-dimensional tooth-facing bonding surface and a bracket body for an individual patient with the aid of a computer having access to a library of three-dimensional virtual descriptions of bracket features, the method comprising the steps of:

determining a three-dimensional shape of a tooth-facing surface of a first graphically displayed three-dimensional virtual orthodontic bracket object responsive to data describing a three-dimensional shape of a corresponding lingual portion of a tooth surface of a specific tooth of a specific patient, the three-dimensional shape of the lingual tooth-facing surface of the first graphically displayed three-dimensional bracket object precisely matching the three-dimensional shape of the corresponding lingual portion of the tooth surface of the specific tooth to conform thereto;

deriving from the library at least one graphically displayed three-dimensional virtual representation of a bracket feature for the first graphically displayed three-dimensional virtual orthodontic bracket object; and modifying the first graphically displayed three-dimensional virtual orthodontic bracket object to include the at least one graphically displayed three-dimensional virtual representation of a bracket feature to thereby form an updated three-dimensional virtual orthodontic bracket object configured to be used for shaping of the three-dimensional tooth-facing bonding surface and of the bracket body of the custom orthodontic lingual bracket.

18. A method as defined in claim 17, wherein the step of modifying includes virtually adding the at least one graphically displayed three-dimensional virtual representation of a bracket feature in its entirety to the first graphically displayed three-dimensional virtual orthodontic bracket object to thereby form the updated three-dimensional virtual orthodontic bracket object.

19. A method as defined in claim 17, wherein the step of modifying includes subtracting the at least one graphically displayed three-dimensional virtual representation of a feature in its entirety from the first graphically displayed three-dimensional virtual orthodontic bracket object to thereby form the updated three-dimensional virtual orthodontic bracket object.

20. A method as defined in claim 17,
wherein the feature comprises an archwire slot for receiving an archwire;
wherein the modified first graphically displayed three-dimensional virtual orthodontic bracket object defines a second graphically displayed three-dimensional virtual orthodontic bracket object; and
wherein the method further comprises the step of shaping the custom orthodontic lingual bracket according to the second graphically displayed three-dimensional virtual orthodontic bracket object, the step of shaping comprising shaping of the three-dimensional bonding surface and of the bracket body of the custom orthodontic lingual bracket.

21. A method as defined in claim 20, wherein the first graphically displayed three-dimensional virtual orthodontic bracket object comprises a bonding pad having an increased thickness adjacent the slot for receiving the archwire.

22. A method as defined in claim 17, wherein the first graphically displayed three-dimensional virtual orthodontic bracket object comprises a bonding pad, and wherein the at least one three-dimensional virtual representation of a feature comprises an archwire slot.

23. A method of designing for custom-shaping a custom orthodontic lingual bracket including a three-dimensional tooth-facing bonding surface and a bracket body for an individual patient, with the aid of a computer having access to a library of three-dimensional virtual descriptions of bracket features, the method comprising the steps of:
determining a three-dimensional shape of a lingual tooth-facing surface of a first graphically displayed three-dimensional virtual orthodontic bracket object responsive to data describing a three-dimensional shape of a corresponding lingual portion of a tooth surface of a specific tooth of a specific patient, the three-dimensional shape of the lingual tooth-facing surface of the first graphically displayed three-dimensional bracket object substantially matching the three-dimensional shape of the corresponding lingual portion of the tooth surface of the specific tooth to conform substantially thereto, the first three-dimensional virtual orthodontic bracket object including a bonding pad;
deriving from the library at least one graphically displayed three-dimensional virtual representation of a bracket feature for the first graphically displayed three-dimensional virtual orthodontic bracket object; and
modifying the first graphically displayed three-dimensional virtual orthodontic bracket object to include the at least one graphically displayed three-dimensional virtual representation of a bracket feature, the modified first graphically displayed three-dimensional virtual orthodontic bracket object defining a second three-dimensional virtual orthodontic bracket object configured to be used for shaping of the three-dimensional tooth-facing bonding surface and of the bracket body of the custom orthodontic lingual bracket during manufacturing of the custom orthodontic lingual bracket.

24. A method as defined in claim 23,
wherein the bonding pad has a greater thickness in medial portions than in peripheral portions thereof; and
wherein the method further comprises the step of manufacturing the three-dimensional bonding surface of the custom orthodontic lingual bracket and the bracket body of the custom orthodontic bracket according to the second three-dimensional virtual orthodontic bracket object.

25. A method of designing for manufacturing a custom orthodontic lingual bracket for an individual patient with the aid of a computer having access to a library of virtual descriptions of bracket features, the method comprising the steps of:
determining a three-dimensional shape of a lingual tooth-facing surface of a first graphically displayed virtual orthodontic bracket object at least substantially matching a corresponding three-dimensional shape of a lingual portion of a tooth surface of a tooth of the individual patient, the first graphically displayed three-dimensional virtual orthodontic bracket object including a bonding pad;
deriving from the library at least one graphically displayed virtual representation of a feature for the first graphically displayed three-dimensional virtual orthodontic bracket object, the at least one graphically displayed virtual representation of a bracket feature including one or more of the following: a virtual archwire slot and a virtual auxiliary bracket device; and
modifying the first graphically displayed virtual orthodontic bracket object to include the at least one graphically displayed virtual representation of a bracket feature, the modified first graphically displayed virtual orthodontic bracket object defining a second virtual orthodontic bracket object configured to be used for custom shaping of a three-dimensional bonding surface and a shaping a bracket body of the custom lingual orthodontic bracket during manufacturing of the custom orthodontic lingual bracket.

26. A method as defined in claim 25,
wherein modifying includes subtracting the at least one graphically displayed virtual representation of a feature from the first graphically displayed three-dimensional virtual orthodontic lingual bracket object; and
wherein the method further comprises the step of manufacturing the three-dimensional bonding surface and the bracket body of the custom lingual orthodontic bracket according to the second three-dimensional virtual orthodontic lingual bracket object.

27. A method of designing and manufacturing a custom lingual orthodontic bracket including a tooth-facing bonding surface and a bracket body, the method comprising the steps of:
storing a digital representation of portions of a dentition of a specific patient in a computer memory;
determining a tooth-facing surface conforming substantially to corresponding three-dimensional surfaces of a lingual portion of a tooth of a specific patient to thereby form and graphically display a virtual object;
receiving a graphically displayed virtual description of a non-custom bracket feature from the computer memory;
graphically designing a custom orthodontic lingual bracket using a computer, the designing including the step of virtually combining the graphically displayed virtual description of the non-custom bracket feature and the graphically displayed virtual object associated with the determined tooth-facing surface into a combined three-dimensional object describing the custom orthodontic lingual bracket so that the custom orthodontic lingual bracket design incorporates a shape of the determined tooth-facing surface and a shape of the non-custom bracket feature;
exporting digital data representing the designed custom lingual orthodontic bracket from the computer to a manufacturing system for manufacturing the custom orthodontic lingual bracket, the exporting including exporting digital data representing the combined three-dimensional object; and manufacturing the custom orthodontic lingual bracket at least substantially in its entirety to include the tooth-facing bonding surface and the bracket body, responsive to the digital data.

28. A method as defined in claim 27, wherein the graphically displayed virtual object associated with the determined tooth-facing surface comprises a virtual bracket bonding pad object having the determined tooth-facing surface; and wherein the step of graphically designing further includes forming and graphically displaying the virtual bracket bonding pad object.

29. A method as defined in claim 28, wherein the step of forming the graphically displayed virtual bonding pad object includes:

forming a virtual tooth-surface object having zero thickness and having a substantially same three-dimensional shape of the lingual portion of the tooth of the patient to be covered by a corresponding physical custom bonding pad, to thereby form the virtual tooth-facing surface of the graphically displayed virtual bonding pad object.

30. A method as defined in claim 29, wherein the virtual three-dimensional tooth-surface object is a first graphically displayed virtual tooth-surface object, and wherein the step of forming a virtual bracket bonding pad object further includes:

forming a second virtual tooth-surface object having zero thickness and having a substantially same three-dimensional shape of the first virtual tooth-surface object and positioned offset therefrom to thereby form a virtual lingual facing surface of the virtual bracket bonding pad object located opposite of the tooth-facing surface of the virtual bracket bonding pad object.

31. A method as defined in claim 28, wherein the step of designing further includes graphically forming a virtual archwire slot in a virtual bracket body of the graphically displayed virtual non-custom bracket feature; and wherein the step of designing further includes the steps of graphically positioning and orienting the virtual archwire slot relative to the tooth-facing surface of the virtual bracket bonding pad object.

32. A method as defined in claim 28, wherein the step of designing further includes:

graphically shifting a virtual location of a virtual bracket body of the graphically displayed virtual non-custom bracket feature relative to the tooth-facing surface of the graphically displayed virtual bracket bonding pad object to thereby merge the virtual bracket body with the virtual bracket bonding pad object.

33. A method as defined in claim 32, wherein portions of the virtual bracket body of the graphically displayed virtual non-custom bracket feature initially extend through the graphically displayed virtual bracket bonding pad object responsive to the merging of the virtual bracket body with the virtual bracket bonding pad object; and wherein the step of designing further includes the step of virtually subtracting the portions of the virtual bracket body extending through the virtual bracket bonding pad object.

34. A method as defined in claim 28, wherein the graphically displayed virtual non-custom bracket feature comprises a virtual bracket body; and wherein the step of designing further includes:

graphically shifting a virtual location of the virtual bracket body relative to a tooth surface of a virtual tooth model so that portions of the virtual bracket body initially extend through portions of the virtual tooth, and virtually subtracting the portions of the virtual bracket body extending through the virtual tooth.

35. A method of designing and manufacturing a custom orthodontic lingual bracket including a tooth-facing surface and a bracket body, the method comprising the steps of:

receiving a three-dimensional virtual description of a selected bracket bonding pad of a plurality of bracket bonding pads stored in memory of a computer, the virtual description of the selected bracket bonding pad to be graphically displayed;

receiving a three-dimensional virtual description of a selected bracket body of a plurality of bracket bodies stored in the computer memory;

graphically displaying the virtual description of the bracket body separate from the graphically displayed virtual description of the bracket bonding pad;

graphically combining the graphically displayed virtual description of the bracket bonding pad and the graphically displayed virtual description of the bracket body by the computer to form a consolidated three-dimensional virtual object providing a virtual description of the custom orthodontic lingual bracket;

exporting digital data representing the graphically displayed virtual description of the custom orthodontic lingual bracket from the computer to a manufacturing system for manufacturing the custom orthodontic lingual bracket; and manufacturing the custom orthodontic lingual bracket to include shaping the tooth-facing surface and the bracket body of the custom orthodontic lingual bracket together responsive to the digital data.

\* \* \* \* \*